(12) United States Patent
Olsson et al.

(10) Patent No.: US 9,061,981 B2
(45) Date of Patent: Jun. 23, 2015

(54) DIPHENYL SUBSTITUTED CYCLOHEXANE DERIVATIVES, USEFUL AS MODULATORS OF THE ESTROGEN RECEPTORS BETA

(75) Inventors: Roger Olsson, Bunkeflostrand (SE); Birgitte Lund, Ballerup (DK); Magnus Gustafsson, Frederiksberg (DK)

(73) Assignee: Acadia Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 14/236,237

(22) PCT Filed: Aug. 1, 2012

(86) PCT No.: PCT/EP2012/065026
§ 371 (c)(1),
(2), (4) Date: May 14, 2014

(87) PCT Pub. No.: WO2013/017619
PCT Pub. Date: Feb. 7, 2013

(65) Prior Publication Data
US 2014/0275284 A1    Sep. 18, 2014

Related U.S. Application Data

(60) Provisional application No. 61/513,725, filed on Aug. 1, 2011.

(30) Foreign Application Priority Data

Aug. 1, 2011 (EP) ...................... 11176144

(51) Int. Cl.
| | |
|---|---|
| A61K 31/075 | (2006.01) |
| A61K 31/045 | (2006.01) |
| C07C 43/02 | (2006.01) |
| C07C 43/225 | (2006.01) |
| C07C 39/42 | (2006.01) |

(52) U.S. Cl.
CPC .............. *C07C 43/225* (2013.01); *C07C 39/42* (2013.01); *C07C 2101/14* (2013.01)

(58) Field of Classification Search
USPC ........................... 514/717, 729; 568/661, 745
See application file for complete search history.

(56) References Cited

U.S. PATENT DOCUMENTS

| | | |
|---|---|---|
| 2006/0122278 A1 | 6/2006 | Olsson et al. |
| 2009/0131510 A1 | 5/2009 | Olsson et al. |
| 2011/0003815 A1 | 1/2011 | Ogawa et al. |
| 2011/0046237 A1 | 2/2011 | Olsson et al. |
| 2012/0088825 A1 | 4/2012 | Olsson et al. |

FOREIGN PATENT DOCUMENTS

| | | |
|---|---|---|
| CN | 1997618 A | 7/2007 |
| WO | WO-2005/108337 A2 | 11/2005 |
| WO | WO-2007/056500 A2 | 5/2007 |
| WO | WO-2007056500 A2 | 5/2007 |
| WO | WO-2008/033894 A2 | 3/2008 |
| WO | WO-2008033894 A2 | 3/2008 |
| WO | WO-2009/055734 A1 | 4/2009 |
| WO | WO-2009055734 A1 | 4/2009 |

OTHER PUBLICATIONS

International Search Report PCT/ISA/210 for PCT/EP2012/065026 dated Aug. 27, 2012.
H. Östlund et al. "Estrogen Receptor Gene Expression in Relation to Neuropsychiatric Disorders"; Annals of the New York Academy of Sciences, vol. 1007, p. 54-63; 2003.
C. Behl "Estrogen can protect neurons: modes of action"; Journal of Steroid Biochemistry & Molecular Biology, vol. 83, p. 195-197; 2003.
H. Brauner-Osborne, et al. "Pharmacology of muscarinic acetylcholine receptor subtypes (m1—m5): high throughput assays in mammalian cells"; European Journal of Pharmacology, vol. 295, p. 93-102; 1996.
E. Burstein, et al. "The ras-related GTPase rac1 regulates a proliferative pathway selectively utilized by G-protein coupled receptors"; Oncogene, vol. 17, p. 1617-1623; 1998.
K. Carlson, et al. "Peripheral Neuropathy with Microtubule-Targeting Agents: Occurrence and Management Approach"; Clinical Breast Cancer, vol. 11, p. 73-81; 2011.
J. Couse, et al. "Estrogen Receptor Null Mice: What Have We Learned and Where Will They Lead Us?"; Endocrine Reviews, vol. 20, p. 358-417; 1999.
M. Erlandsson, et al. "Role of oestrogen receptors α and β in immune organ development and in oestrogen-mediated effects on thymus"; Immunology, vol. 103, p. 17-25; 2001.

(Continued)

*Primary Examiner* — Samantha Shterengarts
(74) *Attorney, Agent, or Firm* — Harness, Dickey & Pierce, P.L.C.

(57) ABSTRACT

Disclosed herein are novel di-aromatic compounds of the general formula (I). Also pharmaceutical compositions comprising the novel compounds and the use of the novel compounds in treatment and prevention of diseases and disorders related to estrogen receptors are disclosed. Furthermore, methods for treating and preventing diseases and disorders related to estrogen receptors by administration of the novel compounds are disclosed.

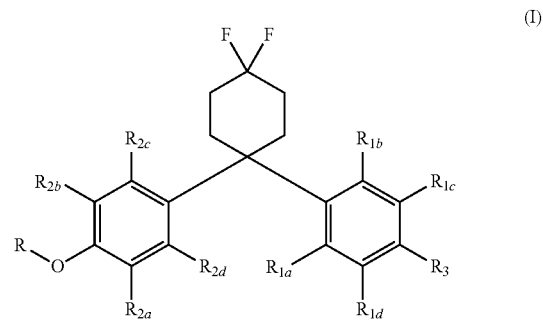

12 Claims, 10 Drawing Sheets

(56) References Cited

OTHER PUBLICATIONS

R. Evans; "The Steroid and Thyroid Hormone Receptor Superfamily" Science, vol. 240, p. 889-95; 1988.
L. Gardell, et al. "Differential modulation of inflammatory pain by a selective estrogen receptor beta agonist"; European Journal of Pharmacology, vol. 592, p. 158-159; 2008.
G. Greene, et al. "Sequence and Expression of Human Estrogen Receptor Complementary DNA"; Science, vol. 231, p. 1150-1154; 1986.
T. Greene, et al. "Protective Groups in Organic Synthesis, Third Edition"; 1999.
S. Green, et al. "Human oestrogen receptor cDNA: sequence, expression and homology to v-erb-A"; Nature, vol. 320, p. 134-9; 1986.
H. Harris "Evaluation of an Estrogen Receptor-β Agonist in Animal Models of Human Disease"; Endocrinology, vol. 144, p. 4241-9; 2003.
S. Hewitt, et al. "Estrogen receptor transcription and transactivation Estrogen receptor knockout mice: what their phenotypes reveal about mechanisms of estrogen action"; Breast Cancer Research, vol. 2, p. 345-352; 2000.
S. Kim, et al. "An experimental model for peripheral neuropathy produced by segmental spinal nerve ligation in the rat"; Pain, vol. 50, p. 355-363; 1992.
K. Koehler, e al. "Reflections on the Discovery and Significance of Estrogen Receptor β"; Endocrine Reviews, vol. 26, p. 465-478; 2005.
G. Kuiper, et al. "The novel estrogen receptor-β subtype: potential role in the cell—and promoter-specific actions of estrogens and antiestrogens"; Federation of European Biochemical Societies Letters, vol. 410, p. 87-90; 1997.
G. Kuiper, et al. "Cloning of a novel estrogen receptor expressed in rat prostate and ovary"; Proceedings of the National Academy of Sciences, vol. 93, p. 5925-5930; 1996.
M. Lindberg, et al. "Two Different Pathways for the Maintenance of Trabecular Bone in Adult Male Mice"; Journal of Bone and Mineral Research, vol. 17, p. 555-562; 2002.
J. Matthews, et al. "Estrogen Signaling: A Subtle Balance Between ERα and ERβ"; Molecular Interventions, vol. 3, p. 281-292; 2003.
M. Naguib, et al. "MDA7: a novel selective agonist for CB2 receptors that prevents allodynia in rat neuropathic pain models"; British Journal of Pharmacology, vol. 155, p. 1104-1116; 2008.
S. Nilsson, et al. "Oestrogen Receptors and Selective Oestrogen Receptor Modulators: Molecular and Cellular Pharmacology"; Basic & Clinical Pharmacology & Toxicology, vol. 96, p. 15-25; 2005.
S. Nilsson, et al. "Development of subtype-selective oestrogen receptor-based therapeutics"; Nature Reviews Drug Discovery, vol. 10, p. 778-792; 2011.
C. Osborne, et al. "Estrogen-Receptor Biology: Continuing Progress and Therapeutic Implications"; Journal of Clinical Oncology, vol. 23, p. 1616-1622; 2005.
M. Osterlund, et al. "Estrogen receptors in the human forebrain and the relation to neuropsychiatric disorders"; Progress in Neurobiology, vol. 64, p. 251-267; 2001.
C. Patrone, et al. "Regulation of Postnatal Lung Development and Homeostasis by Estrogen Receptor β"; Molecular and Cellular Biology, vol. 23, p. 8542-8552; 2003.
F. Piu, et al. "Identification of novel subtype selective RAR agonists"; Biochemical Pharmacology, vol. 71, p. 156-162; 2005.
F. Piu, et al. "Dissection of the cytoplasmic domains of cytokine receptors involved in STAT and Ras dependent proliferation" Oncogene vol. 21, p. 3579-3591; 2002.
F. Piu, et al. "β-arrestin 2 modulates the activity of nuclear receptor RAR β2 through activation of ERK2 kinase"; Oncogene vol. 25, p. 218-229; 2006.
K. Saijo, et al. "An ADIOL-ERβ-CtBP Transrepression Pathway Negatively Regulates Microglia-Mediated Inflammation"; Cell, vol. 145, p. 584-595; 2011.
L. Wang, et al. "Morphological abnormalities in the brains of estrogen receptor β knockout mice"; Proceedings of the National Academy of Sciences, vol. 98, p. 2792-2796; 2001.
L. Wang, et al. "Estrogen receptor (ER)β knockout mice reveal a role for ERβ in migration of cortical neurons in the developing brain"; Proceedings of the National Academy of Sciences, vol. 100, p. 703-708; 2003.
S. Windahl, et al. "Elucidation of estrogen receptor function in bone with the use of mouse models"; TRENDS in Endocrinology & Metabolism, vol. 13, p. 195-200; 2002.
P. Wise "Estrogens and neuroprotection"; TRENDS in Endocrinology & Metabolism, vol. 13, p. 229-230; 2002.
International Search Report PCT/ISA210 for PCT/EP2012/065026 dated Aug. 27, 2012.
International Preliminary Report on Patentability dated Feb. 13, 2014 issued in corresponding International Application No. PCT/EP2012/065026.

DIPHENYL SUBSTITUTED CYCLOHEXANE DERIVATIVES, USEFUL AS MODULATORS OF THE ESTROGEN RECEPTORS BETA

CROSS-REFERENCE TO RELATED APPLICATIONS

This application is a national phase under 35 U.S.C. §371 of PCT International Application No. PCT/EP2012/065026 which has an International filing date of Aug. 1, 2012, which claims priority to European patent application number EP 11176144.1 filed Aug. 1, 2011 and U.S. provisional patent application No. 61/513,725 filed Aug. 1, 2011.

FIELD OF THE INVENTION

This invention relates to the fields of organic chemistry, pharmaceutical chemistry, biochemistry, molecular biology and medicine. In particular it relates to compounds which are modulators of the estrogen receptor beta and are useful in the prevention and/or treatment of diseases and disorders related to the estrogen receptor beta.

DESCRIPTION OF RELATED ART

Estrogen receptors (ERs) belong to the family of nuclear hormone receptors. Nuclear hormone receptors define a superfamily of ligand activated transcription factors (Evans, 1988, Science 240:889). Members of this family are typically characterized by the presence of conserved modular domains: a zinc finger DNA binding domain (DBD) triggers the interaction of the receptor with specific response elements at the DNA site, a ligand binding domain (LBD) adjacent to the DBD, and two transcriptional activation domains AF-1 and AF-2 ligand-independent and liganddependent, respectively (Nilsson, 2002, SERMs: Research and clinical applications, Eds: Humana Press Inc, 3). Upon ligand binding to the receptor, a conformational change occurs within the LBD bringing the AF-2 domain in closer proximity and allowing for the recruitment of co-activators. Co-activators create a physical interaction between the nuclear hormone receptor and components of the transcriptional machinery, establishing transcriptional modulation of target genes.

Two estrogen receptor subtypes have been identified: ER alpha (ERα, NR3A1) (Green, 1986, Nature 320:134; Greene, 1986, Science 231:1150) and ER beta (ERβ, NR3A2) (Kuiper, 1996, PNAS 93:5925). Both receptors bind to the endogenus natural ligand 17β estradiol with comparable high affinity and modulate the transcriptional activity of target genes through classical estrogen response elements (reviewed in Nilsson, 2005, Bas Clin Pharm Tox, 96:15). More recently, it has been demonstrated that estrogen receptors can mediate non classical actions (reviewed in Osborne, 2005, J Clin Oncol 8:1616): (1) non classical transcriptional regulation in which ERs function as co-activators on alternate regulatory DNA sequences, (2) non genomic or membrane-initiated steroid signaling in which ERs evoke rapid cytoplasmic signaling, and (3) crosstalk with Receptor Tyrosine Kinases (RTKs). Interestingly enough, their ligand binding domains (LBD) only share 56% amino acid identity which suggests that they might accommodate different ligands and thus mediate different or even opposite effects (Kuiper, 1997, FEBS Lett, 410:87). Moreover, the distribution pattern of the two receptors is quite different (reviewed in Mathews, 2003, Mol Interv 3:281). Both ERs are widely distributed both peripherally and in the brain, displaying distinct and sometimes overlapping patterns in a variety of tissues. ERα is expressed primarily in the uterus, liver, kidney and heart. On the other hand, ERβ is present mainly in the ovary, prostate, lung, gastrointestinal tract, bladder, hematopoietic and central nervous system (CNS). ERβ specific localization in the CNS includes the hippocampus and thalamus (Osterlund, 2001, Prog Neurobiol 64:251; Ostlund, 2003, Ann NY acad Sci 1007:54). ERα and ERβ are co-expressed in the mammary gland, epididymis, thyroid, adrenal, bone and the dorsal root ganglia of the spinal cord and the cerebral cortex of the brain.

The characterization of mice lacking ERα or ERβ has provided insight into the physiology of estrogen receptors (reviewed in Hewitt, 2000, Breast Cancer Res 2:345; Couse, 1999, Endoc Rev 20:358). Both ERα male and female null mice are infertile because of dysfunction in spermatogenesis and ovulation, respectively. In addition, null females display a lack of sexual behavior, increased aggression and infanticide. Null male exhibit normal mounting behavior but a complete lack of intromission and ejaculation. They also show reduced aggression. In contrast, ERβ null female mice are subfertile with reduced littermates. Male counterparts show no apparent defects in their reproductive tract. The neuroendocrine system is significantly altered in ERα null mice in contrast to ERβ null mice which do not show any impairment. Moreover, the knock-out of ERα in mice leads to absence of breast tissue development, lower bone density and impaired glucose tolerance. Knock out studies of ERβ led to controversial results with some studies being unable to see an effect on bone density (Lindberg, 2002, J Bone Min Res 17:555), whereas other reports suggested an increase in trabecular bone volume in females only due to decreased bone resorption (reviewed in Windahl, 2002, Trends Endoc Metab, 13:195). Interestingly enough, morphological alterations in the brains of mice lacking ERβ are evident (Wang, 2001, PNAS 98:2792) associated with impaired neuronal survival (Wang, 2003, PNAS 100:703), and lead to speculate that ERβ could have an important role in protecting from neurodegenerative disorders such as Alzheimer and Parkinson diseases, and potentially from those resulting of trauma and cardiovascular insults. This is further supported by experimental studies indicating a neurotrophic and neuroprotective role for estrogens (reviewed in Wise, 2002, Trends Endocrinol Metab 13:229; Behl, 2003, J Steroid Biochem Mol Biol 83:195).

More recently, the use of a relatively selective ERβ agonist has unraveled a prominent role in inflammation for this subtype (Harris, 2003, Endoc 144:4241 and Saijo et al Cell 145, 584-595). Beneficial effects were seen in animal models of inflammatory bowel disease and adjuvant-induced arthritis. Indeed, ERβ is expressed both in the intestine and in immune cells. Moreover, ERβ null studies have suggested a role in thymus function (Erlandsson, 2001, Immunol 103:17) as well as in pulmonary inflammation (Patrone, 2003, Mol Cell Biol 25:8542). Interestingly though, no effects associated with classical estrogen function was evident through the use of this ERβ agonist (Harris, 2003, Endoc 144:4241). In particular, that ligand was inactive in mammotrophy, bone density and ovulation in vivo assays. This data is to a certain extent in contrast to a variety of studies including human polymorphisms, knock-out animals, tissue distribution, that argue for a role of ERβ in bone and ovulation homeostasis. Other therapeutic roles for selective ERβ agonists have also been proposed including prostate and breast cancer, autoimmune diseases, colon cancer, malignancies of the immune system, neurodegeneration, cardiovascular function, bone function (reviewed in Koehler, 2005, Endocr Reviews, DOI 10.1210).

These findings suggest that the discovery of compounds that modulate activity of Estrogen receptor beta would be beneficial in treating many diseases and disorders associated with Estrogen receptor beta.

The disclosures of all documents referred to throughout this application are incorporated herein by reference.

SUMMARY OF THE DISCLOSURE

One embodiment disclosed herein is a compound of formula (I):

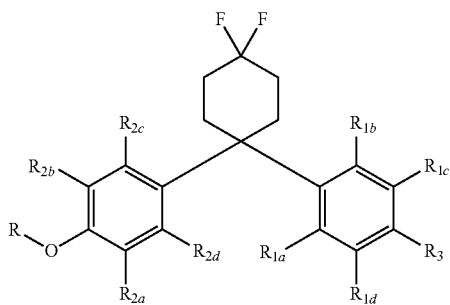

as a single isomer, a mixture of isomers or a racemic mixture of isomers; or a solvate or polymorph thereof, or a metabolite or prodrug thereof, or a pharmaceutically acceptable salt thereof, wherein:

R is selected from the group consisting of hydrogen, $C_{1-6}$ alkyl, $C_{1-6}$ alkenyl, $C_{1-6}$ alkynyl, $C_{3-8}$ cycloalkyl, $C_{3-8}$ cycloalkenyl, substituted or unsubstituted $C_{3-8}$ aryl, substituted or unsubstituted $C_{3-8}$ heteroaryl, substituted or unsubstituted $C_{3-8}$ heteroalicyclyl, $C_{1-6}$ haloalkyl, sulfonyl, —C(=Z)R$_4$, —C(=Z)OR$_4$, —C(=Z)NR$_{4a}$R$_{4b}$, —S(O)NR$_{4a}$R$_{4b}$, —S(O)$_2$NR$_{4a}$R$_{4b}$, —P(=O)(OR$_4$), and —CH$_2$O(C=O)R$_4$, wherein R$_4$, R$_{4a}$ and R$_{4b}$ are selected from the groups defined below;

R$_{1a}$, R$_{1b}$, R$_{1c}$ and R$_{1d}$ are separately selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ alkyl($C_{3-6}$ cycloalkyl), halogen, $C_{1-6}$ haloalkyl, $C_{1-6}$ haloalkoxy, —CN, —C(=Z)R$_4$, —C(=Z)OR$_4$, —C(=Z)NR$_{4a}$R$_{4b}$, —C(R$_4$)=NR$_{4a}$, —NR$_{4a}$R$_{4b}$, —N=CR$_{4a}$R$_{4b}$, —N(R$_4$)—C(=Z)R$_4$, —N(R$_4$)—C(=Z)NR$_{4a}$R$_{4b}$, —S(O)NR$_{4a}$R$_{4b}$, —S(O)$_2$NR$_{4a}$R$_{4b}$, —N(R$_4$)—S(=O)R$_4$, —N(R$_4$)—S(=O)$_2$R$_4$, —OR$_4$, —SR$_4$, and —OC(=Z)R$_4$, wherein each R$_4$, R$_{4a}$ and R$_{4b}$ is separately selected from the groups defined below; or two of R$_{1a}$, R$_{1b}$, R$_{1c}$, R$_{1d}$ and R$_3$ (as defined below) on adjacent carbons, taken together with the two intervening carbons to which they are attached, form a $C_{3-6}$ cycloalkenyl, aryl, heteroaryl or $C_{2-6}$ heterocycloalkyl group;

R$_{2a}$, R$_{2b}$, R$_{2c}$ and R$_{2d}$ are separately selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ alkyl($C_{3-6}$ cycloalkyl), halogen, $C_{1-6}$ haloalkyl, $C_{1-6}$ haloalkoxy, —CN, —C(=Z)R$_4$, —C(=Z)OR$_4$, —C(=Z)NR$_{4a}$R$_{4b}$, —C(R$_4$)=NR$_{4a}$, —NR$_{4a}$R$_{4b}$, —N=CR$_{4a}$R$_{4b}$, —N(R$_4$)—C(=Z)R$_4$, —N(R$_4$)—C(=Z)NR$_{4a}$R$_{4b}$, —S(O)NR$_{4a}$R$_{4b}$, —S(O)$_2$NR$_{4a}$R$_{4b}$, —N(R$_4$)—S(=O)R$_4$, —N(R$_4$)—S(=O)$_2$R$_4$, —OR$_4$, —SR$_4$, and —OC(=Z)R$_4$, wherein each R$_4$, R$_{4a}$ and R$_{4b}$ is separately selected from the groups defined below; or two R$_{2a}$, R$_{2b}$, R$_{2c}$ and R$_{2d}$ on adjacent carbons taken together with the two intervening carbons to which they are attached, form a $C_{3-6}$ cycloalkenyl, aryl, heteroaryl or $C_{2-6}$ heterocycloalkyl group;

R$_3$ is selected from the group consisting of hydrogen, $C_{1-6}$ alkyl, $C_{2-6}$ alkenyl, $C_{3-6}$ cycloalkyl, $C_{3-6}$ cycloalkenyl, halogen, —CN, —SR$_4$, sulfonyl, —C(=Z)NR$_{4a}$R$_{4b}$, —C(=O)R$_4$, —NR$_{4a}$R$_{4b}$, —C(Z)OR$_4$, and $C_{1-6}$ haloalkyl, wherein R$_4$, R$_{4a}$ and R$_{4b}$ are selected from the groups defined below;

R$_4$, R$_{4a}$ and R$_{4b}$ are separately selected from the group consisting of hydrogen, $C_{1-6}$ alkyl, $C_{2-6}$ alkenyl, $C_{2-6}$ alkynyl, $C_{3-6}$ cycloalkyl, $C_{3-6}$ cycloalkenyl, aryl, heteroaryl, $C_{2-6}$ heterocycloalkyl; or R$_{4a}$ and R$_{4b}$ taken together with the nitrogen to which they are attached, form a $C_{2-6}$ heterocycloalkyl group; or R$_{4a}$ and R$_{4b}$ taken together with the carbon to which they are attached, form a $C_{3-6}$ cycloalkyl or $C_{2-6}$ heterocycloalkyl group;

Z is O (oxygen) or S (sulfur); and wherein each of said alkyl, alkenyl, alkynyl, cycloalkyl, alkoxy cycloalkenyl, aryl, heteroaryl and $C_{2-6}$ heterocycloalkyl mentioned above for the different options for R, R$_{1a}$, R$_{1b}$, R$_{1c}$, R$_{1d}$, R$_{2a}$, R$_{2b}$, R$_{2c}$, R$_{2d}$, R$_3$, R$_4$, R$_{4a}$ and R$_{4b}$ independently is optionally substituted by one or more substituent(s) independently selected from the group consisting of —CN, halogen, haloalkyl, —O($C_{1-6}$ alkyl), —NR$_{4a}$R$_{4b}$, —S($C_{1-6}$ alkyl), —O($C_{1-6}$ haloalkyl).

An aspect of this invention is a compound selected from the group consisting of:

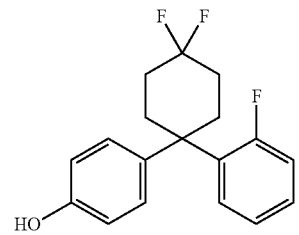

8

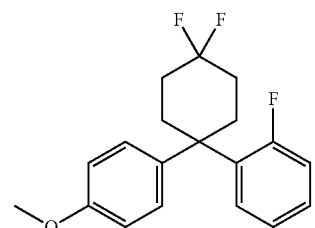

9

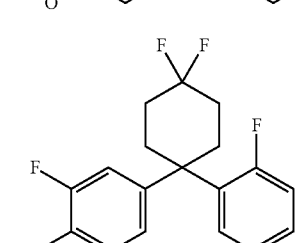

10

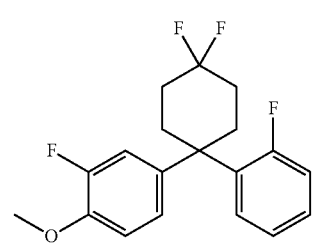

11

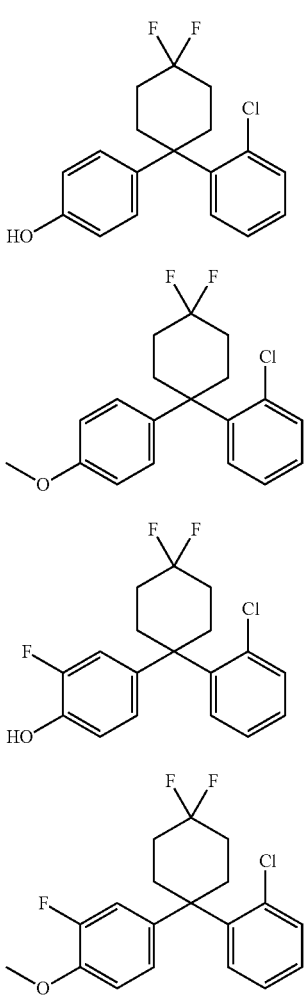

DETAILED DESCRIPTION OF THE INVENTION

Definitions

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

All patents, patent applications, published patent applications and other publications mentioned herein are incorporated by reference in their entirety.

The term "subject" refers to an animal, preferably a mammal, and most preferably a human, who is the object of treatment, observation or experiment. The mammal may be selected from the group consisting of mice, rats, rabbits, guinea pigs, dogs, cats, sheep, goats, cows, primates, such as monkeys, chimpanzees, and apes, and humans.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician, and includes alleviation of the symptoms of the disease being treated.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

As used herein, "$EC_{50}$" refers to a dosage, concentration or amount of a particular test compound that elicits a dose-dependent response at 50% of maximal expression of a particular response that is induced, provoked or potentiated by the particular test compound, in an assay that measures such response for example but not limited to the R-SAT™ and Luciferase assays described herein.

The expression "separately selected from the group consisting of" means herein that each of the substituents or other component given before the expression may be selected separately and independently from the list given after the expression, regardless of what the other substituents are. For example, "$R_{1a}$, $R_{1b}$, $R_{1c}$ and $R_{1d}$ are separately selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ alkyl($C_{3-6}$ cycloalkyl), halogen, $C_{1-6}$ haloalkyl, $C_{1-6}$ haloalkoxy, —CN, —C(=Z) $R_4$, —C(=Z)$OR_4$, —C(=Z)$NR_{4a}R_{4b}$, —C($R_4$)=$NR_{4a}$, —$NR_{4a}R_{4b}$, —N=$CR_{4a}R_{4b}$, —N($R_4$)—C(=Z)$R_4$, —N($R_4$)—C(=Z)$NR_{4a}R_{4b}$, —S(O)$NR_{4a}R_{4b}$, —S(O)$_2$ $NR_{4a}R_{4b}$, —N($R_4$)—S(=O)$R_4$, —N($R_4$)—S(=O)$_2R_4$, —$OR_4$, —$SR_4$, and —OC(=Z)$R_4$" means that each of $R_{1a}$, $R_{1b}$, $R_{1c}$ and $R_{1d}$ is selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ alkyl($C_{3-6}$ cycloalkyl), halogen, $C_{1-6}$ haloalkyl, $C_{1-6}$ haloalkoxy, —CN, —C(=Z)$R_4$, —C(=Z) $OR_4$, —C(=Z)$NR_{4a}R_{4b}$, —C($R_4$)=$NR_{4a}$, —$NR_{4a}R_{4b}$, —N=$CR_{4a}R_{4b}$, —N($R_4$)—C(=Z)$R_4$, —N($R_4$)—C(=Z) $NR_{4a}R_{4b}$, —S(O)$NR_{4a}R_{4b}$, —S(O)$_2NR_{4a}R_{4b}$, —N($R_4$)—S (=O)$R_4$, —N($R_4$)—S(=O)$_2R_4$, —$OR_4$, —$SR_4$, and —OC (=Z)$R_4$ completely independently of what the other three of $R_{1a}$, $R_{1b}$, $R_{1c}$ and $R_{1d}$ are, and similarly "each halogen separately is selected from chloro, bromo and fluoro" means that one halogen may be, e.g. chloro while the other(s) may be any choice of chloro, bromo and fluoro.

Unless otherwise indicated, whenever a group is described as being "optionally substituted" or when a group is described as being "unsubstituted or substituted" that group may be unsubstituted or substituted with one or more group(s) individually and independently selected from alkyl, alkenyl, alkynyl, cycloalkyl, aryl, heteroaryl, heteroalicyclic, hydroxyl, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, *Protective Groups in Organic Synthesis*, 3rd Ed., John Wiley & Sons, New York, N.Y., 1999, which is incorporated herein in its entirety.

As used herein, "$C_{m-n}$" in which "m" and "n" are integers refers to the number of carbon atoms in an alkyl, alkenyl or alkynyl group or the number of carbon atoms in the ring of a cycloalkyl or cycloalkenyl group. That is, the alkyl, alkenyl, alkynyl, ring of the cycloalkyl or ring of the cycloalkenyl can contain from "m" to "n", inclusive, carbon atoms. Thus, for example, a "$C_{1-4}$ alkyl" group refers to all alkyl groups having from 1 to 4 carbons, that is, $CH_3$—, $CH_3CH_2$—, $CH_3CH_2CH_2$—, $CH_3CH(CH_3)$—, $CH_3CH_2CH_2CH_2$—, $CH_3CH_2CH(CH_3)$— and $(CH_3)_3CH$—. If no "m" and "n" are designated with regard to an alkyl, alkenyl, alkynyl, cycloalkyl or cycloalkenyl group, the broadest range described herein for these definitions is to be assumed.

As used herein, "alkyl" refers to a straight or branched hydrocarbon chain fully saturated (no double or triple bonds) hydrocarbon group. An alkyl group of this invention may comprise from 1 to 20 carbon atoms. An alkyl group herein may also be of medium size having 1 to 10 carbon atoms. It is presently preferred that an alkyl group of this invention be a lower alkyl having 1 to 5 carbon atoms. Examples of alkyl groups include, without limitation, methyl, ethyl, n-propyl, isopropyl, n-butyl, iso-butyl, sec-butyl, tert-butyl, amyl, tert-amyl, hexyl, heptyl, octyl, nonyl, decyl, undecyl and dodecyl.

As used herein, "alkoxy" refers to the formula —OR wherein R is an alkyl is defined as above, e.g. methoxy, ethoxy, n-propoxy, 1-methylethoxy (isopropoxy), nbutoxy, iso-butoxy, sec-butoxy, tert-butoxy, amoxy, tert-amoxy and the like.

An alkyl group of this invention may be substituted or unsubstituted. When substituted, hydrogen atoms are replaced by substituent group(s) that is(are) one or more group(s) independently selected from cycloalkyl, aryl, heteroaryl, heteroalicyclyl, hydroxy, protected hydroxyl, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, trihalomethanesulfonyl, —$NR_{1a}R_{1b}$ and protected amino.

"Lower alkylene groups" are straight chained tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$(CH_2)_4$—) groups.

As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group may be optionally substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, alkoxy, aryloxy, acyl, ester, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl. Preferred aryl groups are $C_{4-8}$ aryl groups, i e 4 to 8 membered aryl rings.

As used herein, "heteroaryl" refers to a monocyclic or multicyclic aromatic ring system (a ring system with fully delocalized pi-electron system), one or two or more fused rings that contain(s) one or more heteroatoms, that is, an element other than carbon, including but not limited to, nitrogen, oxygen and sulfur. Examples of heteroaryl rings include, but are not limited to, furan, thiophene, phthalazine, pyrrole, oxazole, thiazole, imidazole, pyrazole, isoxazole, isothiazole, triazole, thiadiazole, pyridine, pyridazine, pyrimidine, pyrazine and triazine. A heteroaryl group may be optionally substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, alkoxy, aryloxy, acyl, ester, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on a heteroaryl group may form a non-aromatic ring fused to the aryl group, including a cycloalkyl, cycloalkenyl, cycloalkynyl, and heterocyclyl. Preferred heteroaryl groups are $C_{2-7}$ heteroaryl groups, i e 3 to 8 membered heteroaryl rings.

"Aralkyl groups" are aryl groups connected, as substituents, via a lower alkylene group. The aryls groups of aralkyl may be substituted or unsubstituted. Examples include but are not limited to benzyl, substituted benzyl, 2-phenylethyl, 3-phenylpropyl and naphtylalkyl.

"Heteroaralkyl groups" are to be understood as heteroaryl groups connected, as substituents, via a lower alkylene group. The heteroaryl groups of heteroaralkyl may be substituted or unsubstituted. Examples include but are not limited to 2-thienylmethyl, 3-thienylmethyl, furylmethyl, thienylethyl, pyrrolylalkyl, pyridylalkyl, isoxazollylalkyl, imidazolylalkyl, and their substituted as well as benzo-fused analogs.

As used herein, "alkoxy" and "alkylthio" refers to RO— and RS—, in which R is an alkyl, including lower alkyl.

As used herein, "aryloxy" and "arylthio" refers to RO— and RS—, in which R is an aryl, such as, but not limited to, phenyl.

As used herein, "alkenyl" refers to an alkyl group that contains in the straight or branched hydrocarbon chain one or more double bonds. An alkenyl group of this invention may be unsubstituted or substituted. When substituted, the substituent(s) may be selected from the same groups disclosed above with regard to alkyl group substitution.

As used herein, "alkylidene" refers to a divalent group, such as =CR'R", which is attached to one carbon of another group, forming a double bond. Alkylidene groups include, but are not limited to, methylidene (=$CH_2$) and ethylidene (=$CHCH_3$). As used herein, "arylalkylidene" refers to an alkylidene group in which either R' and R" is an aryl group.

As used herein, "alkynyl" refers to an alkyl group that contains in the straight or branched hydrocarbon chain one or more triple bonds. An alkynyl group of this invention may be unsubstituted or substituted. When substituted, the substituent(s) may be selected from the same groups disclosed above with regard to alkyl group substitution.

As used herein, "acyl" refers to an "RC(=O)—" group with R as defined above.

As used herein, "cycloalkyl" refers to a completely saturated (no double bonds) mono- or multi-cyclic hydrocarbon ring system. Cycloalkyl groups of this invention may range from $C_3$ to $C_{10}$, in other embodiments it may range from $C_3$ to $C_6$. A cycloalkyl group may be unsubstituted or substituted. If substituted, the substituent(s) may be selected from those indicated above with regard to substitution of an alkyl group.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). A cycloalkenyl group of this invention may be unsubstituted or substituted. When substituted, the substituent(s) may be selected from the groups disclosed above with regard to alkyl group substitution.

As used herein, "heteroalicyclic", "heterocycloalkyl" or "heteroalicyclyl" refers to a stable 3 to 18 membered ring which consists of carbon atoms and from one to five heteroatoms selected from the group consisting of nitrogen, oxygen and sulfur. For the purpose of this invention, the "heteroalicyclic", "heterocycloalkyl" or "heteroalicyclyl" may be monocyclic, bicyclic, tricyclic, or tetracyclic ring system, which may include fused or bridged ring systems; and the nitrogen, carbon and sulfur atoms in the "heteroalicyclic", "heterocycloalkyl" or "heteroalicyclyl" may be optionally oxidized; the nitrogen may be optionally quaternized; and the rings may also contain one or more double bonds provided that they do not form a fully delocalized pi-electron system in the rings. The "heteroalicyclic", "heterocycloalkyl" or "heteroalicyclyl" of this invention may be fused with an aryl or a heteroaryl. "Heteroalicyclic", "heterocycloalkyl" or "heteroalicyclyl" groups of this invention may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoro-methanesulfonamido. Examples of such "heteroalicyclic", "heterocycloalkyl" or "heteroalicyclyl" include but are not limited to, azepinyl, acridinyl, carbazolyl, cinnolinyl, dioxolanyl, imidazolinyl, morpholinyl, oxiranyl, piperidinyl N-oxide, piperidinyl, piperazinyl, pyrrolidinyl, 4-piperidonyl, pyrazolidinyl, 2-oxopyrrolidinyl, thiamorpholinyl, thiamorpholinyl sulfoxide, and thiamorpholinyl sulfone, 2,3-dihydrobenzofuran, 2,3-dihydrobenzo[b]thiophene, indoline. Preferred heteroalicyclic", "heterocycloalkyl" or "heteroalicyclyl" are stable 3 to 8 membered rings.

The ring systems of the cycloalkyl, heteroalicyclic (heteroalicyclyl) and cycloalkenyl groups may be composed of one ring or two or more rings which may be joined together in a fused, bridged or spiro-connected fashion.

As used herein, "halo" or "halogen" refers to F (fluoro), Cl (chloro), Br (bromo) or I (iodo).

As used herein, "haloalkyl" refers to an alkyl group in which one or more of the hydrogen atoms are replaced by halogen. Such groups include but are not limited to, chloromethyl, fluoromethyl, difluoromethyl, trifluoromethyl, 1-chloro-2-fluoromethyl and 2-fluoroisobutyl.

As used herein, "haloalkoxy" refers to an RO-group in which R is a haloalkyl group. Such groups include but are not limited to, chloromethoxy, fluoromethoxy, difluoromethoxy, trifluoromethoxy and 1-chloro-2-fluoromethoxy and 2-fluoroisobutyoxy.

As used herein, "perhaloalkyl" refers to a $C_{1-2}$ alkyl group where all hydrogens have been replaced by halogens. Examples thereof are trihalomethyl, such as trifluoromethyl.

An "O-carboxy" group refers to a "RC(=O)O—" group with R as defined above.

A "C-carboxy" group refers to a "—C(=O)R" group with R as defined above.

An "acetyl" group refers to a $CH_3C$(=O)— group.

A "trihalomethanesulfonyl" group refers to an "$X_3CSO_2$—" group wherein X is a halogen.

A "cyano" group refers to a "—CN" group.

An "isocyanato" group refers to an "—NCO" group.

A "thiocyanato" group refers to a "—CNS" group.

An "isothiocyanato" group refers to an "—NCS" group.

A "sulfinyl" group refers to an "—S(=O)—R" group with R as defined above.

A "sulfonyl" group refers to an "$SO_2R$" group with R as defined above.

An "S-sulfonamido" group refers to a "—$SO_2NR_{1a}R_{1b}$" group with $R_{1a}$ and $R_{1b}$ as defined above.

An "N-sulfonamido" group refers to a "$RSO_2N(R_{1a})$—" group with R and $R_{1a}$ as defined above.

A "trihalomethanesulfonamido" group refers to an "$X_3CSO_2N(R)$—" group with X as halogen and R as defined above.

An "O-carbamyl" group refers to a "—OC(=O)$NR_{1a}R_{1b}$" group with $R_{1a}$ and $R_{1b}$ as defined above.

An "N-carbamyl" group refers to an "ROC(=O)$NR_{1a}$—" group with $R_{1a}$ and R as defined above.

An "O-thiocarbamyl" group refers to a "—OC(=S)—$NR_{1a}R_{1b}$" group with $R_{1a}$ and $R_{1b}$ as defined above.

An "N-thiocarbamyl" group refers to an "ROC(=S)$NR_{1a}$—" group with $R_{1a}$ and R as defined above.

A "C-amido" group refers to a "—C(=O)$NR_{1a}R_{1b}$" group with $R_{1a}$ and $R_{1b}$ as defined above.

An "N-amido" group refers to a "RC(=O)$NR_{1a}$—" group with R and $R_{1a}$ as defined above.

As used herein, an "ester" refers to a "—C(=O)OR" group with R as defined above.

As used herein, an "amide" refers to a "—C(=O)$NR_{1a}R_{1b}$" group with $R_{1a}$ and $R_{1b}$ as defined above.

Any unsubstituted or monosubstituted amine group on a compound herein can be converted to an amide, any hydroxyl group can be converted to an ester and any carboxyl group can be converted to either an amide or ester using techniques wellknown to those skilled in the art (see, for example, Greene and Wuts, Protective Groups in Organic Synthesis, $3^{rd}$ Ed., John Wiley & Sons, New York, N.Y., 1999).

Where the numbers of substituents is not specified (e.g. haloalkyl), there may be one or more substituents present. For example "haloalkyl" may include one or more of the same or different halogens. As another example, "$C_{1-3}$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As used herein, the phrase "taken together" when referring to two "R" groups means that the "R" groups are joined together to form a cycloalkyl, aryl, heteroaryl or heteroalicyclyl group. For example, without limitation, if $R_{1a}$ and $R_{1b}$ of an $NR_{1a}R_{1b}$ group are indicated to be "taken together," it means that they are covalently bonded to one another at their terminal atoms to form a ring:

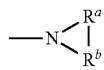

It is understood that, in any compound of this invention having one or more chiral centers, if an absolute stereochemistry is not expressly indicated, then each center may independently be of R-configuration or S-configuration or a mixture thereof. Thus, the compounds provided herein may be enantiomerically pure or be stepreoisomeric or diastereomeric mixtures. In addition it is understood that, in any compound of this invention having one or more double bond(s) generating geometrical isomers that can be defined as E or Z each double bond may independently be E or Z or a mixture thereof. Likewise, all tautomeric forms are also intended to be included.

As used herein, "pharmaceutically acceptable salt" refers to a salt of a compound that does not cause significant irritation to a patient to which it is administered and does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucose amine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methanesulfonates, ethanesulfonates, p-toluenesulfonates and salicylates.

"Polymorphs" and/or "solvates" of the compounds according to the invention a pharmaceutical solid may be used for the purpose of altering the chemical and physical properties, such as melting point, chemical reactivity, apparent solubility, dissolution rate, optical and electrical properties, vapor pressure, and density.

Solvates are crystalline solid adducts containing either stoichiometric or non-stoichiometric amounts of a solvent incorporated within the crystal structure. If the incorporated solvent is water, the solvates are also commonly known as hydrates.

Pharmaceutically acceptable solvates and hydrates are complexes of a compound with one or more solvent of water molecules, or 1 to about 100, or 1 to about 10, or one to about 2, 3 or 4, solvent or water molecules.

As used herein, the term "metabolite" refers to a compound which another compound is converted into upon in vivo administration. Such a metabolite may be a metabolite of a compound that is a metabolite of another compound.

As used herein, the term "prodrug" refers to a compound that might not be pharmaceutically active but that is converted into an active drug upon in vivo administration. The prodrug may be designed to alter the metabolic stability or the transport characteristics of a drug, to mask side effects or toxicity, to improve the flavor of a drug or to alter other characteristics or properties of a drug. Prodrugs are often useful because they may be easier to administer than the parent drug. They may, for example, be bioavailable by oral administration whereas the parent drug is not. The prodrug may also have better solubility than the active parent drug in pharmaceutical compositions. An example, without limitation, of a prodrug would be a compound disclosed herein, which is administered as an ester (the "prodrug") to facilitate absorption through a cell membrane where water solubility is detrimental to mobility but which then is metabolically hydrolyzed to a Hydroxyl (phenol) (the active entity) once inside the cell where water-solubility is beneficial. A further example of a prodrug might be a short peptide (polyaminoacid) bonded to a hydroxyl group where the peptide is metabolized in vivo to release the active parent compound. By virtue of knowledge of pharmacodynamic processes and drug metabolism in vivo, those skilled in the art, once a pharmaceutically active compound is known, can design prodrugs of the compound (see, e.g. Nogrady (1985) *Medicinal Chemistry A Biochemical Approach*, Oxford University Press, New York, pages 388-392)

One embodiment of the present invention relates to a compound of Formula I, as defined above and in the accompanying claims, wherein R is selected from the group consisting of hydrogen and $C_{1-6}$ alkyl; $R_{1a}$, $R_{1b}$, $R_{1c}$ and $R_{1d}$ are separately selected from the group consisting of hydrogen, $C_{1-6}$ alkyl, halogen, $C_{1-6}$ haloalkyl, —CN, and $C_{1-6}$ alkoxy; $R_{2a}$, $R_{2b}$, $R_{2c}$ and $R_{2d}$ are separately selected from the group consisting of hydrogen, $C_{1-6}$ alkyl, halogen, $C_{1-6}$ haloalkyl, —CN, and $C_{1-6}$ alkoxy; and $R_3$ is selected from the group consisting of hydrogen, $C_{1-6}$ alkyl, halogen, and $C_{1-6}$ haloalkyl.

One embodiment of the present invention relates to a compound of Formula I, as defined above and in the accompanying claims, wherein $R_{1a}$, $R_{1b}$, $R_{1c}$ and $R_{1d}$ are separately selected from the group consisting of hydrogen, and halogen; $R_{2a}$, $R_{2b}$, $R_{2c}$ and $R_{2d}$ are separately selected from the group consisting of hydrogen, and halogen; and $R_3$ is selected from the group consisting of hydrogen and halogen.

In one embodiment of the present invention $R_{1b}$ is halogen, for example chloro or fluoro.

In one embodiment of the present invention R is hydrogen or methyl.

In one embodiment of the present invention $R_{1a}$, $R_{1c}$ and $R_{1d}$ are hydrogen; $R_{1b}$ is fluoro or chloro; $R_{2b}$, $R_{2c}$ and $R_{2d}$ are hydrogen; $R_{2a}$ is hydrogen or halogen, for example fluoro; and $R_3$ is hydrogen.

In one embodiment of the present invention the compound is selected from the group consisting of the following compounds:

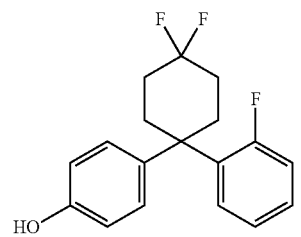

8

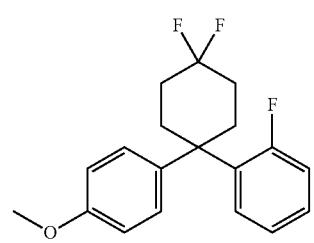

9

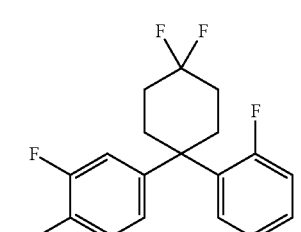

10

-continued

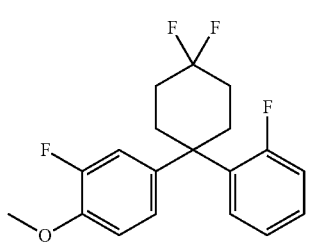

11

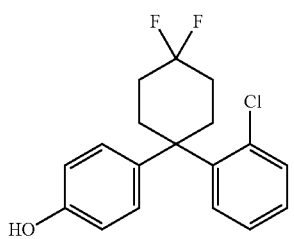

12

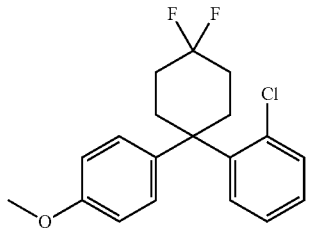

13

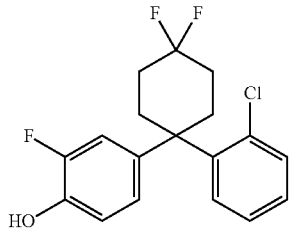

14

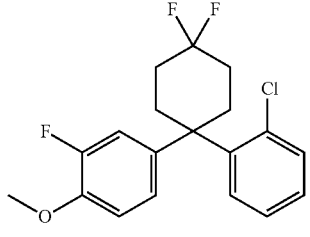

15

In one embodiment of the present invention the compound is selected from the compound of formula 8, compound of formula 9, compound of formula 10 and a compound of formula 14.

In one embodiment of the present invention the compound is the compound of formula 8.

In some embodiments the compound may be a prodrug of compound 8, compound 10, compound 12 or compound 14. In some embodiments the prodrug of compound 8 may be compound 9. In some embodiments the prodrug of compound 10 may be compound 11. In some embodiments the prodrug of compound 12 may be compound 13. In some embodiments the prodrug of compound 14 may be compound 15.

Other embodiments disclosed herein relates to the use of the above described compounds in treatment of a disease, disorder or condition selected from the group consisting of inflammatory bowel syndrome; Crohn's disease; ulcerative proctitis or colitis; prostatic hypertrophy; uterine leiomyomnas; breast carcinoma; endometrial carcinoma; polycystic ovary syndrome; endometrial polyps; benign breast disease; adenomyosis; ovarian carcinoma; melanoma; prostate carcinoma; colon carcinoma; brain tumors including glioblastoma, astrocytoma, glioma, or meningioma; prostatitis; interstitial cystitis; bone density loss including osteoporosis or osteopenia; discholesterolemia; dislipidemia; cardiovascular disease; atherosclerosis; hypertension; peripheral vascular disease; restenosis; vasospasm; neurodegenerative disorders including Alzheimer's disease, Huntington's disease, Parkinson's disease or other dementias resulting in impaired cognitive function (cognition) due to changes in the brain caused by ageing, disease or trauma; spinal cord injury; cognitive decline; stroke; anxiety; depression; vaginal atrophy; vulvar atrophy; atrophic vaginitis; vaginal dryness; pruritus; dyspareunia; frequent urination; urinary incontinence; urinary tract infections; vasomotor symptoms including flushing or hot flashes; arthritis including rheumatoid arthritis, osteoarthritis, or arthropathiesendometriosis; psoriasis; dermatitis; asthma; pleurisy; multiple sclerosis (both with regards to inflammatory aspects and myelination); systemic lupus erthematosis; uveitis; sepsis; hemorrhagic shock; type II diabetes; acute or chronic inflammation; autoimmune diseases; acute or chronis pain, including i.a. allodynia and neuropathic pain such as diabetic peripheral neuropathy; lung disorders including asthma or chronic obstructive pulmonary disease; ophthalmological disorders including glaucoma, dry eye, or macular degeneration; obesity, and free radical induced disease states.

Other embodiments disclosed herein relates to the use of the above described compounds in prevention of a disease or a disorder selected from the group consisting of inflammatory bowel syndrome; Crohn's disease; ulcerative proctitis or colitis; prostatic hypertrophy; uterine leiomyomnas; breast carcinoma; endometrial carcinoma; polycystic ovary syndrome; endometrial polyps; benign breast disease; adenomyosis; ovarian carcinoma; melanoma; prostate carcinoma; colon carcinoma; brain tumors including glioblastoma, astrocytoma, glioma, or meningioma; prostatitis; interstitial cystitis; bone density loss including osteoporosis or osteopenia; discholesterolemia; dislipidemia; cardiovascular disease; atherosclerosis; hypertension; peripheral vascular disease; restenosis; vasospasm; neurodegenerative disorders including Alzheimer's disease, Huntington's disease, Parkinson's disease or other dementias resulting in impaired cognitive function (cognition) due to changes in the brain caused by ageing, disease or trauma; spinal cord injury; cognitive decline; stroke; anxiety; depression; vaginal atrophy; vulvar atrophy; atrophic vaginitis; vaginal dryness; pruritus; dyspareunia; frequent urination; urinary incontinence; urinary tract infections; vasomotor symptoms including flushing or hot flashes; arthritis including rheumatoid arthritis, osteoarthritis, or arthropathiesendometriosis; psoriasis; dermatitis; asthma; pleurisy; multiple sclerosis (both with regards to inflammatory aspects and myelination); systemic lupus erthematosis; uveitis; sepsis; hemorrhagic shock; type II diabetes; acute or chronic inflammation; autoimmune diseases; acute or chronic pain, including i.a. allodynia and neuropathic pain such as diabetic peripheral neuropathy; lung disorders including asthma or chronic obstructive pulmonary disease; ophthalmological disorders including glaucoma, dry eye, or macular degeneration; obesity, and free radical induced disease states.

Another embodiment disclosed herein is a method of treating or preventing a disease, disorder or condition selected from the group consisting of inflammatory bowel syndrome;

Crohn's disease; ulcerative proctitis or colitis; prostatic hypertrophy; uterine leiomyomnas; breast carcinoma; endometrial carcinoma; polycystic ovary syndrome; endometrial polyps; benign breast disease; adenomyosis; ovarian carcinoma; melanoma; prostate carcinoma; colon carcinoma; brain tumors including glioblastoma, astrocytoma, glioma, or meningioma; prostatitis; interstitial cystitis; bone density loss including osteoporosis or osteopenia; discholesterolemia; dislipidemia; cardiovascular disease; atherosclerosis; hypertension; peripheral vascular disease; restenosis; vasospasm; neurodegenerative disorders including Alzheimer's disease, Huntington's disease, Parkinson's disease or other dementias resulting in impaired cognitive function (cognition) due to changes in the brain caused by ageing, disease or trauma; spinal cord injury; cognitive decline; stroke; anxiety; depression; vaginal atrophy; vulvar atrophy; atrophic vaginitis; vaginal dryness; pruritus; dyspareunia; frequent urination; urinary incontinence; urinary tract infections; vasomotor symptoms including flushing or hot flashes; arthritis including rheumatoid arthritis, osteoarthritis, or arthropathiesendometriosis; psoriasis; dermatitis; asthma; pleurisy; multiple sclerosis (both with regards to inflammatory aspects and myelination); systemic lupus erthematosis; uveitis; sepsis; hemorrhagic shock; type II diabetes; acute or chronic inflammation; autoimmune diseases; acute or chronic pain, including i.a. allodynia and neuropathic pain such as diabetic peripheral neuropathy; lung disorders including asthma or chronic obstructive pulmonary disease; ophthalmological disorders including glaucoma, dry eye, or macular degeneration; obesity, and free radical induced disease states; including:

identifying a subject in need of the treating or preventing; and administering to the subject a pharmaceutically effective amount of a compound of formula I:

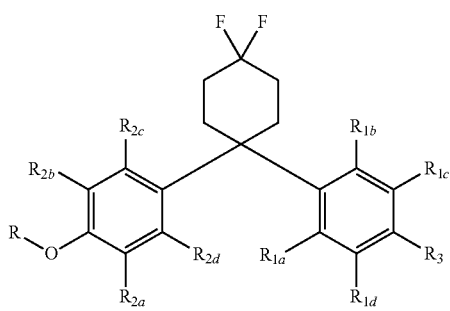

(I)

as a single isomer, a mixture of isomers, or as a racemic mixture of isomers; as a solvate or polymorph; or as metabolite or prodrug or a pharmaceutically acceptable salt thereof, wherein the R groups are defined above and in the accompanying claims.

In some embodiments, the disorder is selected from the group consisting of inflammatory bowel syndrome, Crohn's disease, and ulcerative proctitis or ulcerative colitis.

In some embodiments, the disorder is selected from the group consisting of prostatic hypertrophy, uterine leiomyomnas, breast carcinoma, endometrial carcinoma, polycystic ovary syndrome, endometrial polyps, benign breast disease, adenomyosis, ovarian carcinoma, melanoma, prostate carcinoma, colon carcinoma, and brain tumors including glioblastoma, astrocytoma, glioma, and meningioma.

In some embodiments, the disorder is selected from the group consisting of prostatitis and interstitial cystitis.

In some embodiments, the disorder is bone density loss including osteoporosis and osteopenia.

In some embodiments, the disorder is selected from the group consisting of discholesterolemia and dislipidemia.

In some embodiments, the disorder is selected from the group consisting of cardiovascular disease, atherosclerosis, hypertension, peripheral vascular disease, restenosis and vasospasm.

In some embodiments, the disorder is a neurodegenerative disorder including Alzheimer's disease, Huntington's disease, Parkinson's disease or other dementia resulting in impaired cognitive function (cognition) due to changes in the brain caused by ageing, disease or trauma.

In some embodiments, the disorder is a spinal cord injury.

In some embodiments, the disorder is selected from the group consisting of cognitive decline, stroke, and anxiety.

In some embodiments, the disorder is depression.

In some embodiments, the disorder is selected from the group consisting of vaginal atrophy, vulvar atrophy, atrophic vaginitis, vaginal dryness, pruritus, dyspareunia, frequent urination, urinary incontinence, and urinary tract infections.

In some embodiments, the disorder is one or more vasomotor symptoms including flushing and hot flashes.

In some embodiments, the disorder is endometriosis.

In some embodiments, the disorder is arthritis including rheumatoid arthritis, osteoarthritis, or arthropathies.

In some embodiments, the disorder is selected from the group consisting of psoriasis and dermatitis.

In some embodiments, the disorder is selected from the group consisting of asthma and pleurisy.

In some embodiments, the disorder is selected from the group consisting of multiple sclerosis, systemic lupus erthematosis, uveitis, sepsis, and hemorrhagic shock.

In some embodiments, the disorder is type II diabetes.

In some embodiments, the disorder is selected from the group consisting of acute and chronic inflammation.

In some embodiments, the disorder is an autoimmune disease.

In some embodiments, the disorder is a lung disorders including asthma and chronic obstructive pulmonary disease.

In some embodiments, the disorder is an ophthalmologic disorder including glaucoma, dry eye, and macular degeneration.

In some embodiments, the disorder is a free radical induced disease state.

In some embodiments, the disorder is acute or chronic pain.

In some embodiments, the pain is allodynia.

In some embodiments, the pain is allodynia caused by chemotherapy.

In some embodiments the pain is allodynia caused by a chemotherapeutic agent.

In one embodiment, the pain is neuropathic pain.

In some embodiments, the disorder is obesity.

In some embodiments, the disorder is Parkinson's disease psychosis (PDP).

In some embodiments, the disorder is psychosis in Alzheimer's disease (ADP).

Other embodiments are: a method of hormonal replacement therapy; a method for lowering cholesterol, triglycerides, or LDL level; a method of modulating or specifically agonizing one or more estrogen receptors; and a method of treating impaired cognition or providing neuroprotection; comprising:

identifying a subject in need of hormonal replacement; and administering to the subject a pharmaceutically effective amount of a compound of formula I:

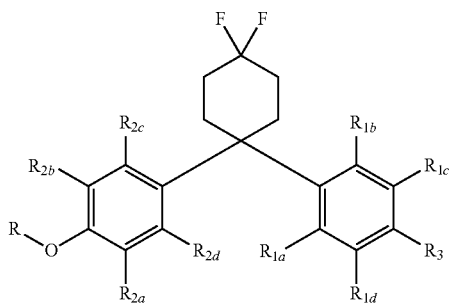
(I)

as a single isomer, a mixture of isomers, or as a racemic mixture of isomers; as a solvate or polymorph; or as metabolite or prodrug or a pharmaceutically acceptable salt thereof, wherein the R groups are defined above and in the accompanying claims.

Another embodiment disclosed herein is a method of preventing conception, comprising administering to a subject a pharmaceutically effective amount of a compound of formula I:

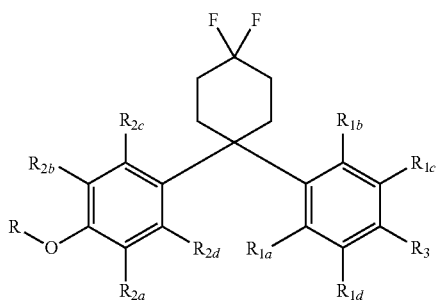
(I)

as a single isomer, a mixture of isomers, or as a racemic mixture of isomers; as a solvate or polymorph; or as metabolite or prodrug or a pharmaceutically acceptable salt thereof, wherein the R groups are defined above and in the accompanying claims.

Another embodiment disclosed herein includes a method of treating or preventing disorders selected from the group consisting of inflammatory bowel syndrome; Crohn's disease; ulcerative proctitis or colitis; prostatic hypertrophy; uterine leiomyomnas; breast carcinoma; endometrial carcinoma; polycystic ovary syndrome; endometrial polyps; benign breast disease; adenomyosis; ovarian carcinoma; melanoma; prostate carcinoma; colon carcinoma; brain tumors including glioblastoma, astrocytoma, glioma, or meningioma; prostatitis; interstitial cystitis; bone density loss including osteoporosis or osteopenia; discholesterolemia; dislipidemia; cardiovascular disease; atherosclerosis; hypertension; peripheral vascular disease; restenosis; vasospasm; neurodegenerative disorders including Alzheimer's disease, Huntington's disease, Parkinson's disease or other dementias resulting in impaired cognitive function (cognition) due to changes in the brain caused by ageing, disease or trauma; spinal cord injury; cognitive decline; stroke; anxiety; depression; vaginal atrophy; vulvar atrophy; atrophic vaginitis; vaginal dryness; pruritus; dyspareunia; frequent urination; urinary incontinence; urinary tract infections; vasomotor symptoms including flushing or hot flashes; arthritis including rheumatoid arthritis, osteoarthritis, or arthropathiesendometriosis; psoriasis; dermatitis; asthma; pleurisy; multiple sclerosis (both with regards to inflammatory aspects and myelination); systemic lupus erthematosis; uveitis; sepsis; hemorrhagic shock; type II diabetes; acute or chronic inflammation; autoimmune diseases; acute or chronic pain, including i.a. allodynia and neuropathic pain such as diabetic peripheral neuropathy; lung disorders including asthma or chronic obstructive pulmonary disease; ophthalmological disorders including glaucoma, dry eye, or macular degeneration; obesity, and free radical induced disease states; comprising:

identifying a subject in need of the treating or preventing; and administering to the subject a pharmaceutically effective amount of a compound of formula I, as a single isomer, a mixture of isomers, or as a racemic mixture of isomers; as a solvate or polymorph; or as metabolite or prodrug or a pharmaceutically acceptable salt thereof, wherein the R groups are defined above and in the accompanying claims.

Another embodiment disclosed herein is a pharmaceutical composition, comprising a pharmaceutically acceptable amount of a compound of formula I and a physiologically acceptable carrier, diluent, or excipient, or a combination two or several of these.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990, which is hereby incorporated by reference in its entirety.

Pharmaceutical compositions for use in accordance with the present disclosure thus may be formulated in conventional manner using one or more physiologically acceptable carriers comprising excipients and auxiliaries, which facilitate processing of the active compounds into preparations, which can be used pharmaceutically. Proper formulation is dependent upon the route of administration chosen. Any of the wellknown techniques, carriers, and excipients may be used as suitable and as understood in the art; e.g., as disclosed in Remington's Pharmaceutical Sciences, cited above.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", Chapter 1, which is hereby incorporated by reference in its entirety). Typically, the dose range of the composition administered to the patient can be from about 0.5 to 1000 mg/kg of the patient's body weight, or 1 to 500 mg/kg, or 10 to 500 mg/kg, or 50 to 100 mg/kg of the patient's body weight. The dosage may be a single one or a series of two or more given in the course of one or more days, as is needed by the patient. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions disclosed herein or a pharmaceutically acceptable salt thereof calculated as the free base, the composition being administered 1 to 4 times per day. Alternatively the compositions disclosed herein may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. In some embodiments, the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, preferably for 30-90% and most preferably for 50-90%.

The amount of composition administered will, of course, be dependent on the subject being treated, on the subject's weight, the severity of the affliction, the manner of administration and the judgment of the prescribing physician.

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

BRIEF DESCRIPTION OF THE DRAWINGS

In the following Examples, references are made to the accompanying drawings on which.

The data for AC-623 in spontaneous locomotor activity are not shown because the behavioral measure did not QC.

Figure 3:
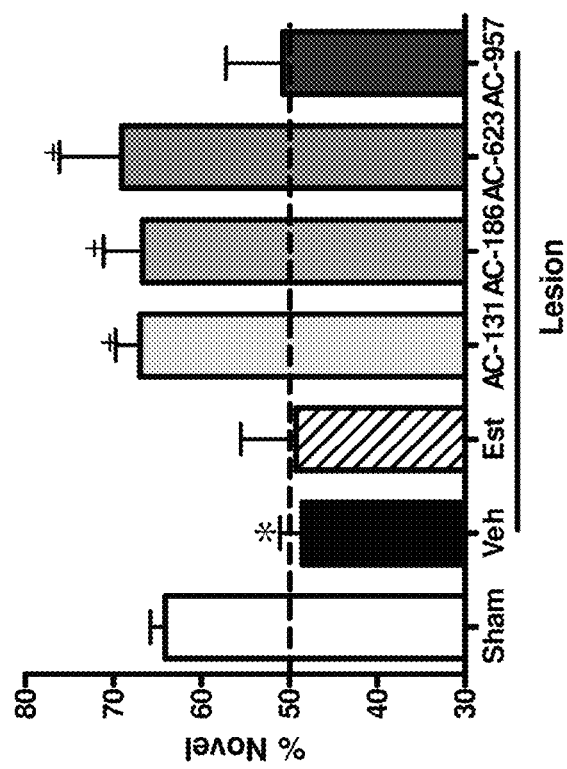

FIG. 3 shows performance on the novel object recognition task for sham (Sham-All Tx) and 6-hydroxydopamine (Lesion) animals. Sham-treated animals showed memory for the previously seen object, thus displaying a significant preference for the novel object during test. In contrast, vehicle-treated 6OHDA animals did not display memory for the previously seen object and thus showed chance performance during test (i.e., no preference for novel object, dashed line). 6OHDA animals treated with Comparative compound 131 (AC-131), Compound 8 (AC-186) or Comparative compound 623 (AC-623), but not Comparative compound 957 (AC-957) or estradiol, showed improved memory for the previously seen object compared with lesioned controls. Thus, treatment with an ERβ agonist protected cognitive performance following 6OHDA infusion. Data were analyzed using a one-way ANOVA followed by Bonferonni's multiple comparison post hic analyses, * indicates a significant difference from sham treated animals, p<0.05. + indicates a significant difference from vehicle/6OHDA, p<0.05.

Figure 4:
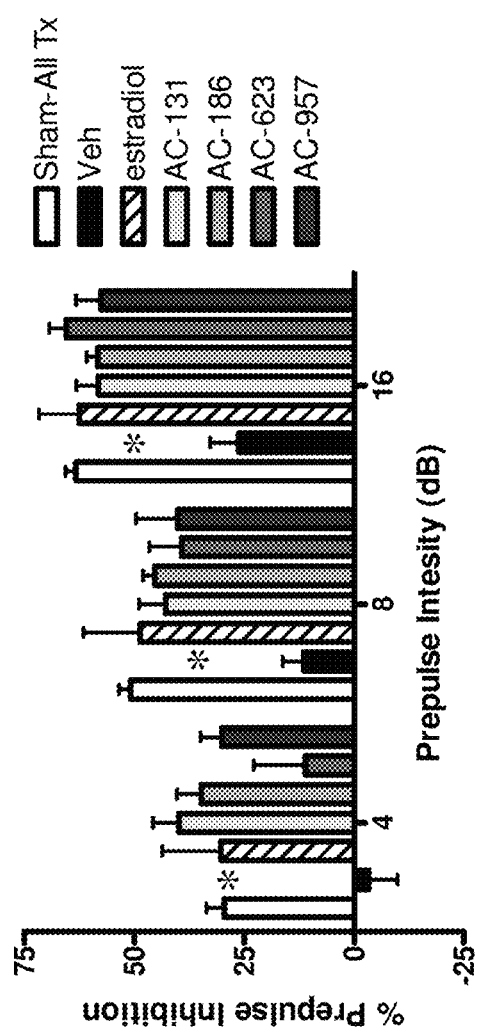

FIG. 4 shows prepulse inhibition performance in sham- and 6OHDA-treated animals. As prepulse intensity increases, animals display an increasing ability to gate startle responding (i.e., increased % prepulse inhibition). A two-way ANOVA shows a significant main effect of treatment condition and a significant main effect prepulse intensity. Bonferroni post hoc analyses for repeated measures showed that vehicle-6OHDA animals showed impaired PPI at all prepulse intensities compared with sham controls. Pretreatment with estradiol, Comparative compound 131 (AC-131), Compound 8 (AC-186), Comparative compound 623 (AC-623) or Comparative compound 957 (AC-957) prevented the 6OHDA-induced deficit in PPI. Data were analyzed using a two-way ANOVA followed by Bonferonni's multiple comparison post hic analyses* indicates a significant difference from sham treated animals, p<0.05. + indicates a significant difference from vehicle/6OHDA, p<0.05.

Figure 5:
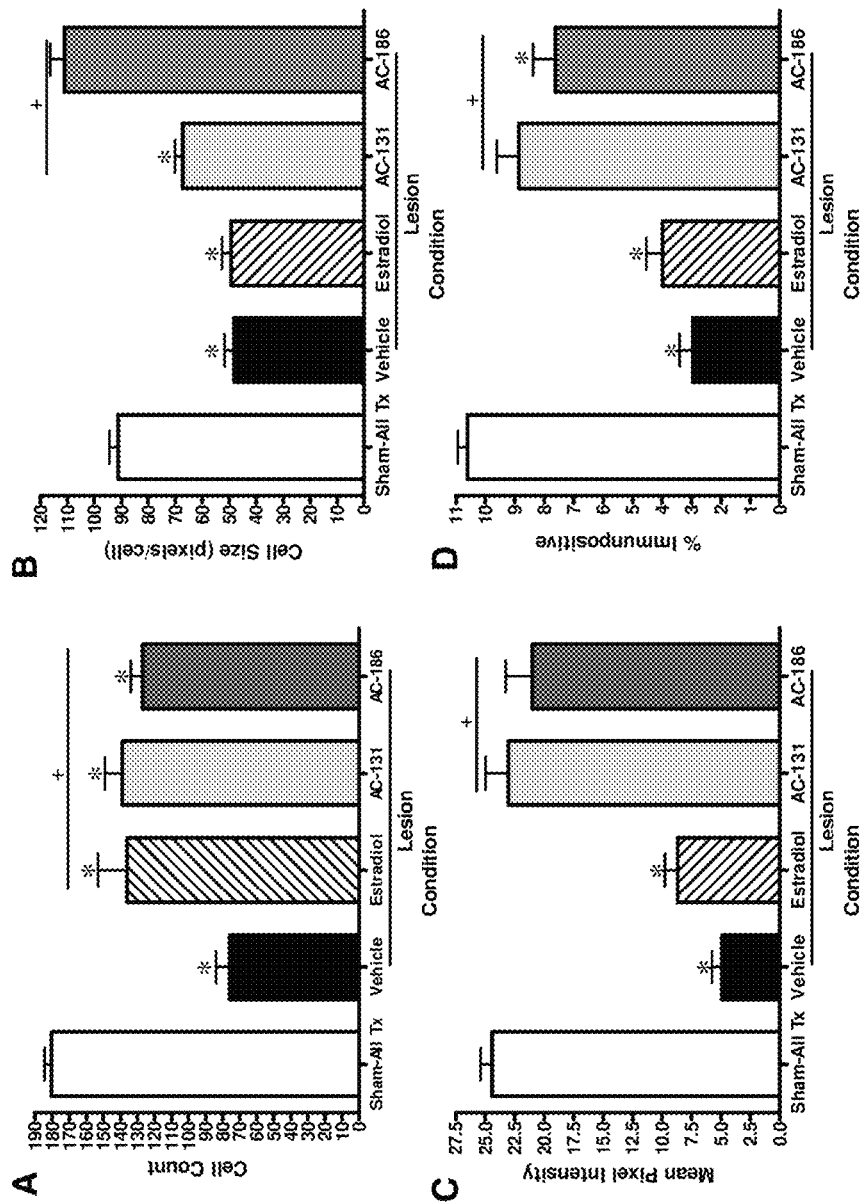

FIG. 5 shows tyrosine hydroxylase immunofluorescence in the SN following sham- or 6OHDA-treatment. 6OHDA resulted in reduced cell counts in the SN (Panel A), reduced percentage of the image that was immunopositive (Panel B), reduced mean cell size (Panel C) and reduced mean pixel intensity of immunofluorescent pixels (Panel D). Treatment with estradiol, Comparative compound 131 (AC-131), Compound 8 (AC-186), Comparative compound 623 (AC-623) or Comparative compound 957 (AC-957) prevented the reduction in cell number, while only the selective ERβ agonists AC-131, AC-186, AC-623 or AC-957 improved percent immunopositive, mean cell size and mean pixel intensity. Data were analyzed with one-way ANOVAs followed by Bonferroni's post hoc comparisons. * indicates a significant difference from Sham, p<0.05; + indicates a significant difference from vehicle/6OHDA, p<0.05.

Figure 6:
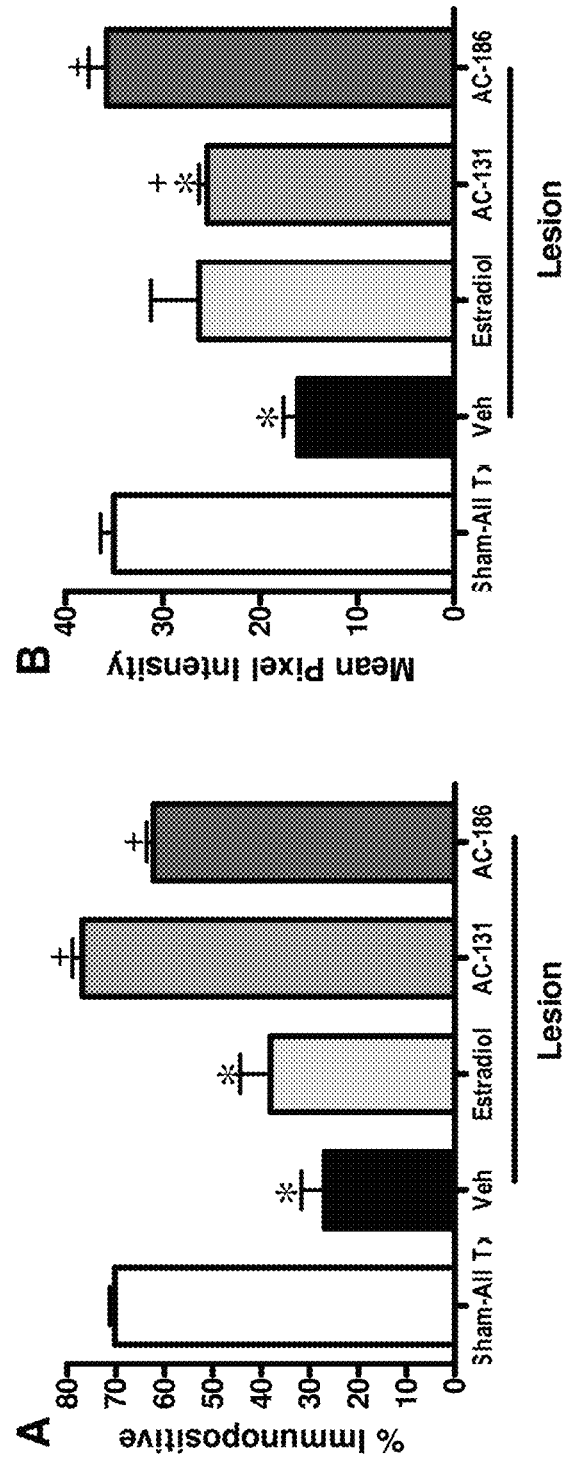

FIG. 6 shows tyrosine hydroxylase immunofluorescence in the STR following sham- or 6OHDA-treatment. 6OHDA resulted in a reduced percentage of the image that was immunopositive (Panel A) and reduced mean pixel intensity of immunofluorescent pixels (Panel B). Treatment with the ERβ-selective agonist Comparative compound 131 (AC-131) or Compound 8 (AC-186) resulted in an increase in percentage of the image that was immunopositive and increased mean pixel intensity compared with lesioned controls, while estradiol treatment did not prevent 6OHDA-induced damage in the striatum. * indicates a significant difference from Sham, p<0.05; + indicates a significant difference from vehicle/6OHDA, p<0.05

Figure 7:
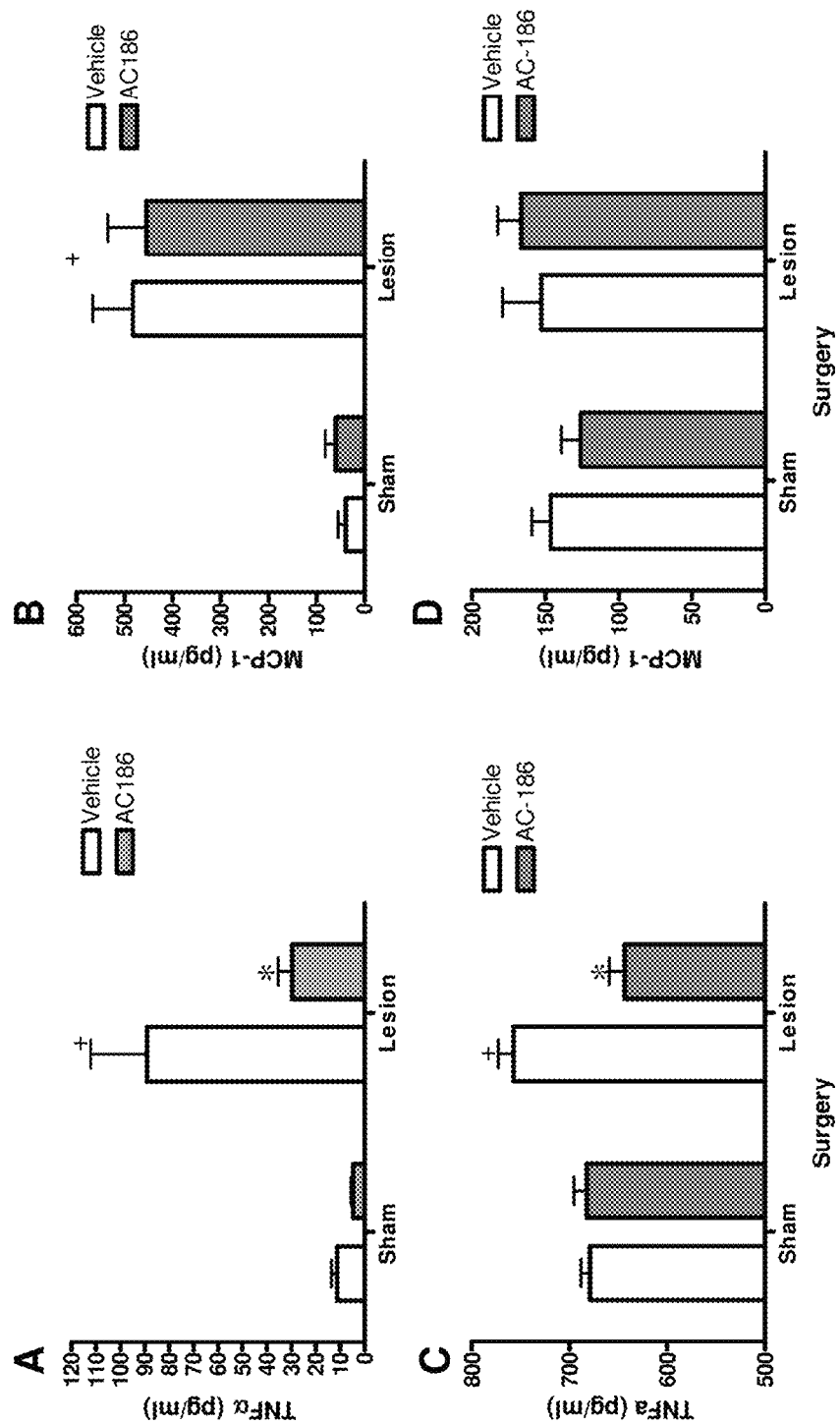

FIG. 7 shows TNFα (Panels A and C) and MCP-1 (Panels B and D) in PBMCs (Panels A and B) or brain homogenate (Panels C and D). 6OHDA lesions increased TNFα in both PBMCs and brain and treatment with Compound 8 (AC-186) blocked this increase. MCP-1 was increased by 6OHDA in PBMCs but not brain, and the increase in PBMCs was not prevented by AC-186. * indicates a significant difference from sham, $p<0.05$, and + indicates a significant difference from vehicle treatment, $p<0.05$.

Figure 1:
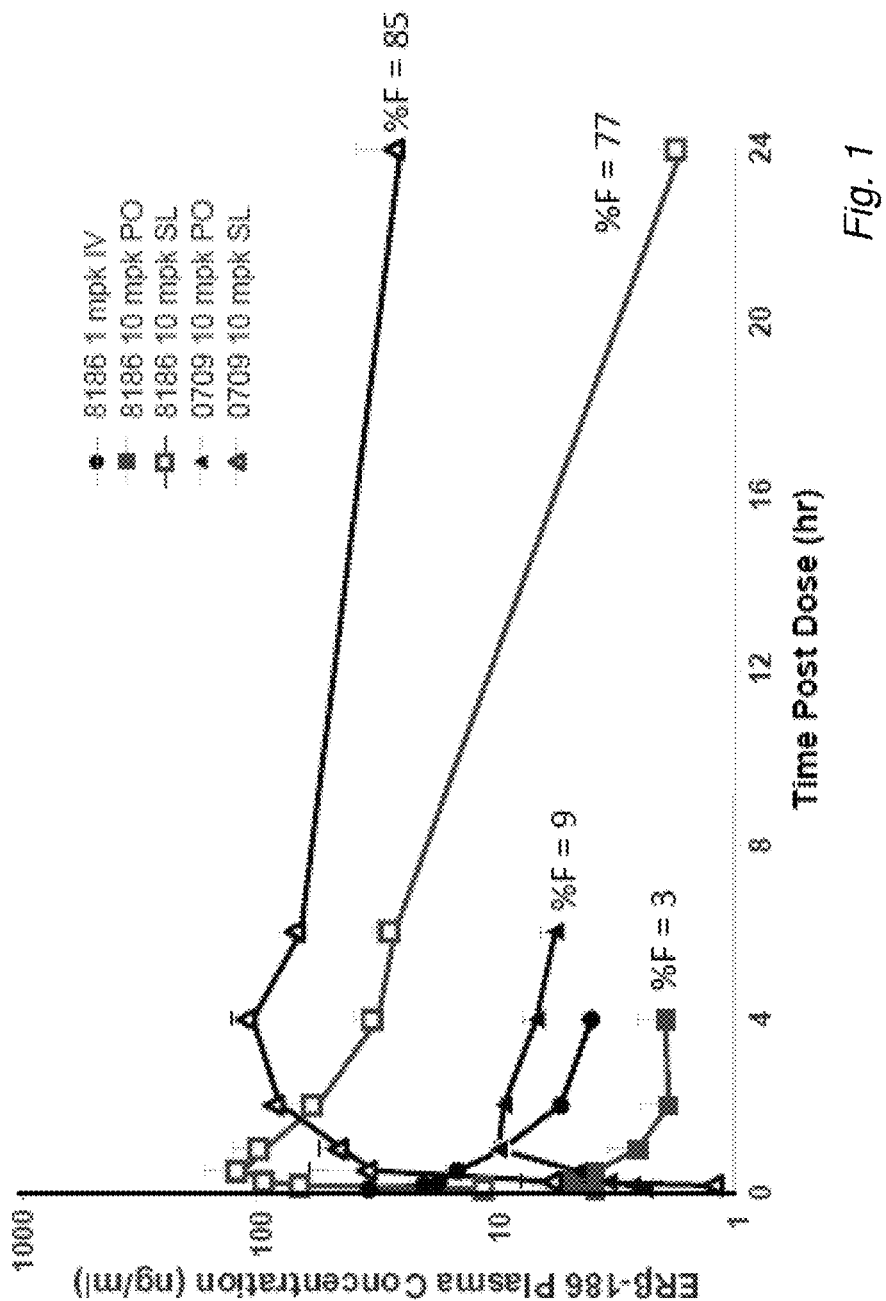
FIG. 1 displays the results of intravenous (IV), oral (PO) and sublingual (SL) administration of Compound 8 (denoted 8186 in this figure) and Compound 9 (denoted 0709 in this figure). In the figure mpk denotes the administered amount in milligram per kilo body weight.
Figure 8:
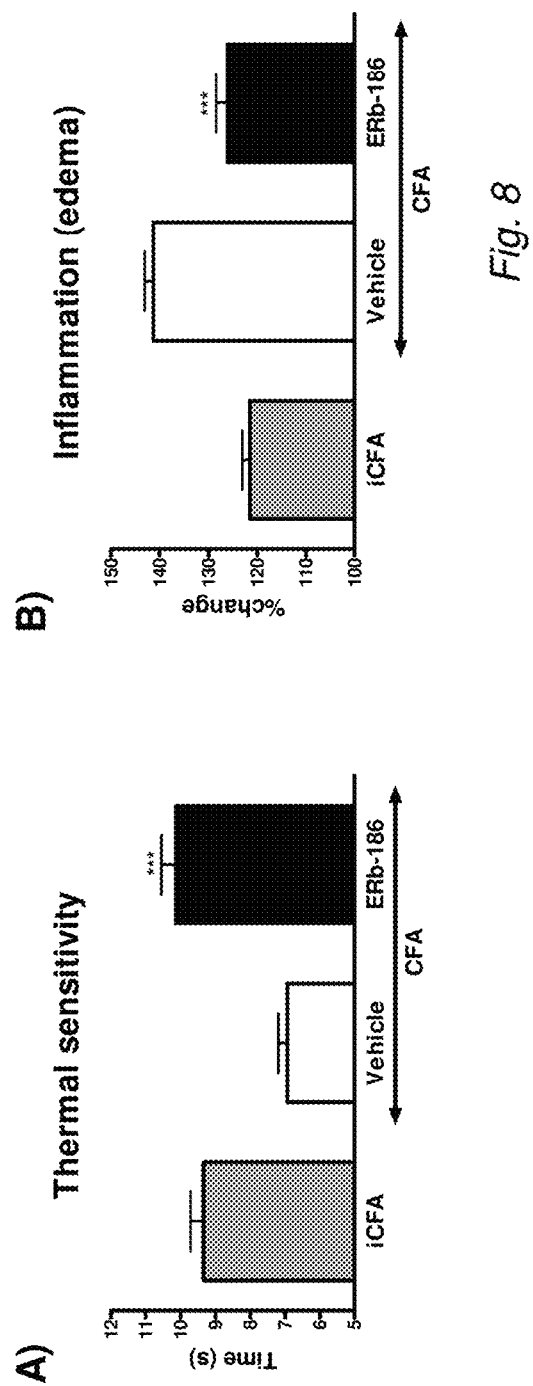

FIG. 8 illustrates that Compound 8 (AC-186, in this Figure denoted ERb-186) inhibits hyperalgesia and inflammation in the CFA model. FIG. 1 (A) shows response to thermal hyperalgesia which was measured using the 52° C. hot plate test. Latencies, expressed in seconds (sec), were defined as the time needed for the animal to remove the treated paw from the hot surface. FIG. 1 (B) shows edema in the treated paw normalized to the change seen in the contralateral (untreated) paw. iCFA, incomplete Freund's Adjuvant. ***$p<0.001$ compared to vehicle.

Figure 9:
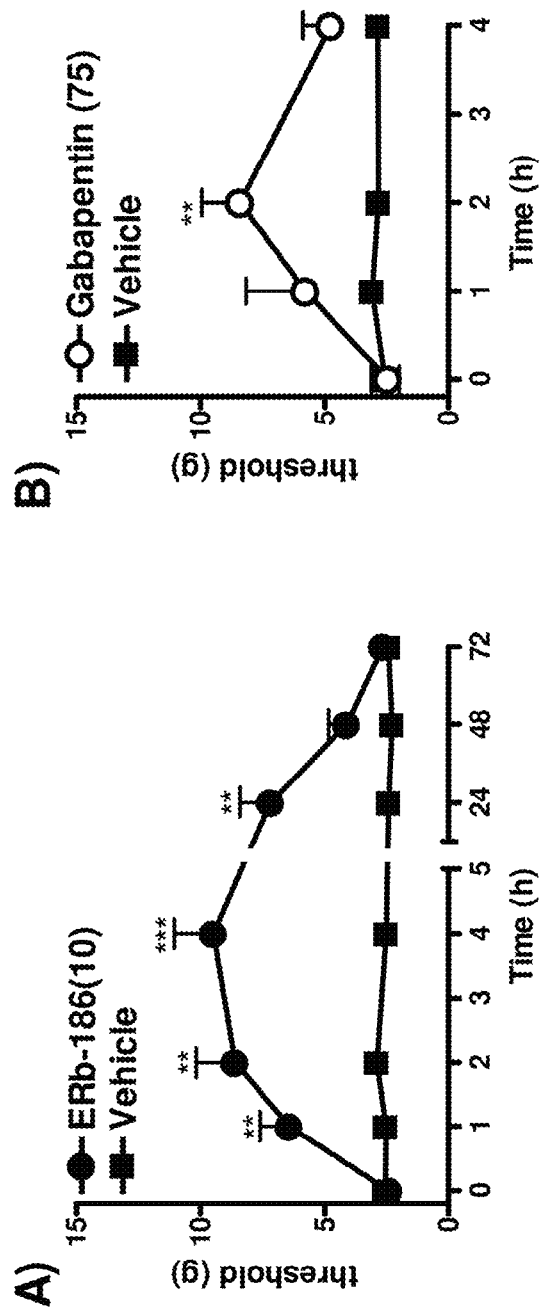

FIG. 9 illustrates that treatment with Compound 8 (AC-186, in this Figure denoted ERb-186) reverses allodynia in the spinal nerve ligation model. Doses are shown as (mg/kg).

Figure 10:
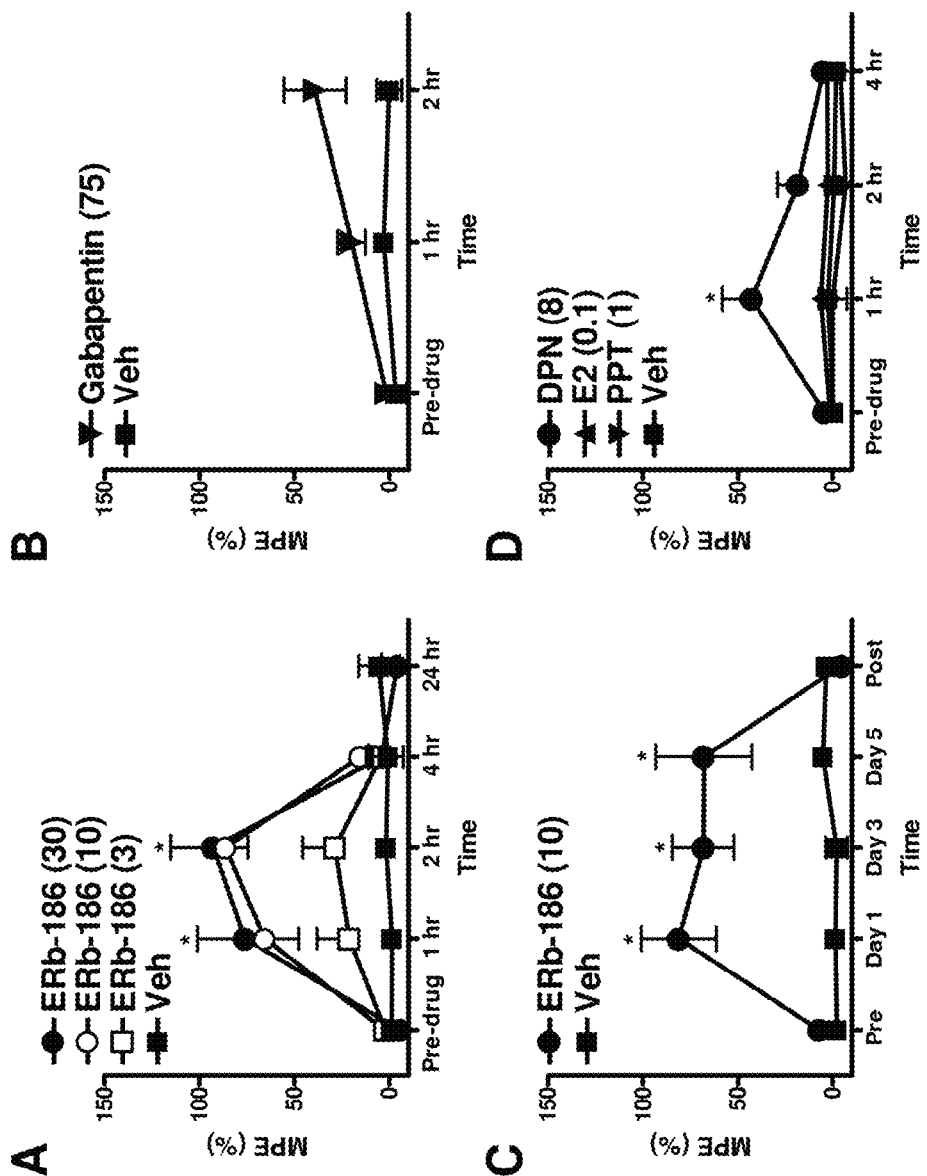

FIG. 10 illustrates that treatment with Compound 8 (AC-186, in this Figure denoted ERb-186) is efficient against Taxol-induced neuropathic pain. Doses are shown as (mg/kg). * $p<0.05$.

EXAMPLES

Embodiments of the present invention are disclosed in further detail in the following examples, which are not in any way intended to limit the scope of the invention.
Synthesis General synthetic routes to the compounds of this invention are shown in Scheme 1. The routes shown are illustrative only and are not intended, nor are they to be construed, to limit the scope of this invention in any manner whatsoever. Those skilled in the art will be able to recognize modifications of the disclosed synthesis and to devise alternate routes based on the disclosures herein; all such modifications and alternate routes are within the scope of this invention. For example, compounds of this invention can be obtained according to the method depicted in Scheme 1.

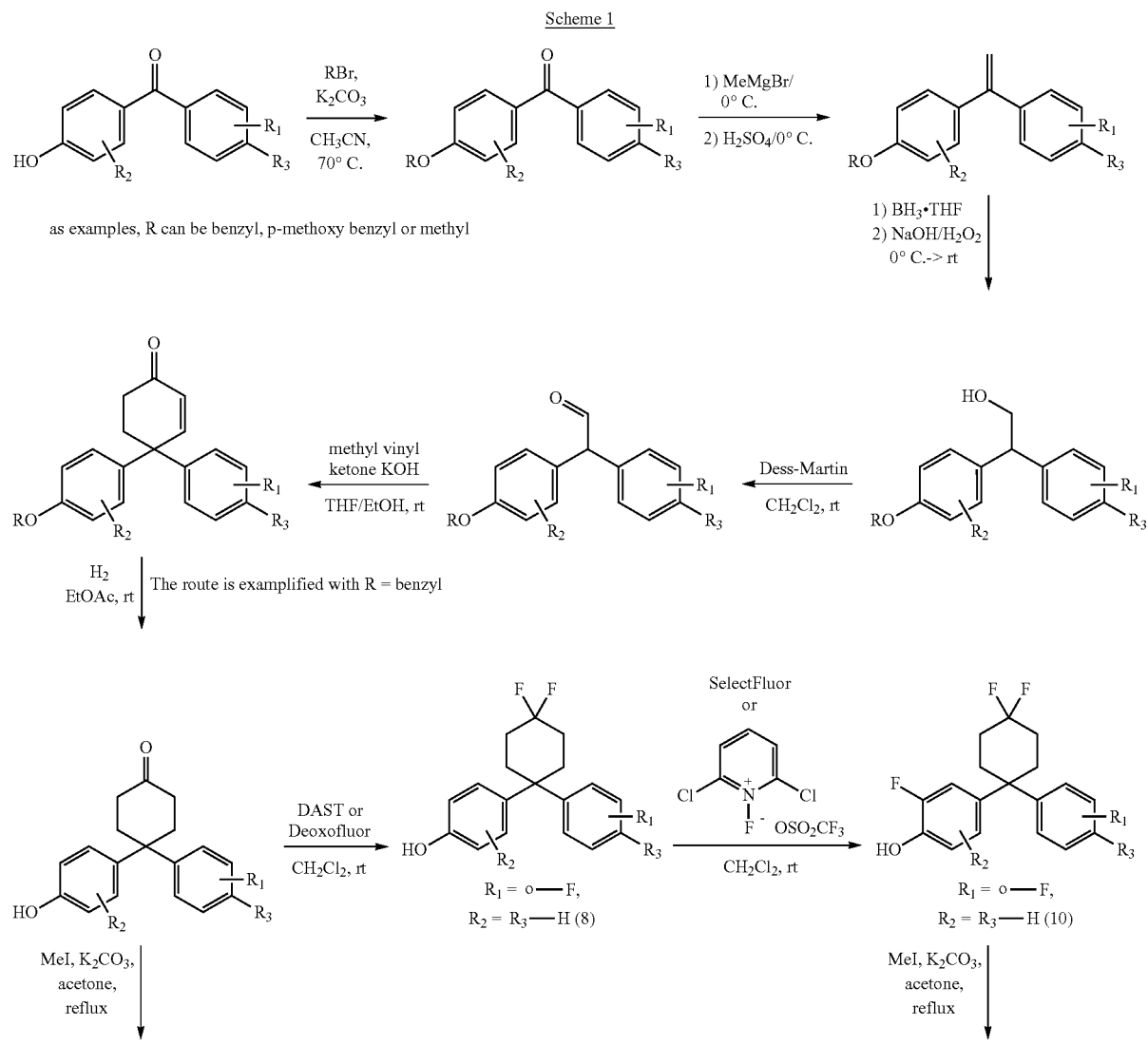

-continued

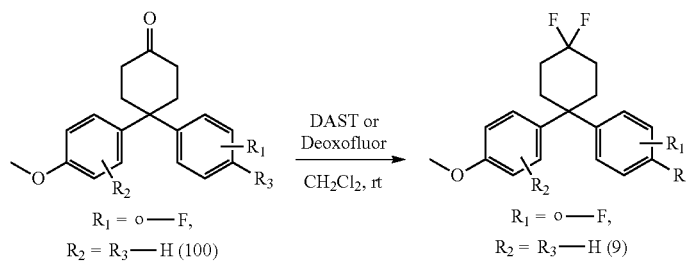
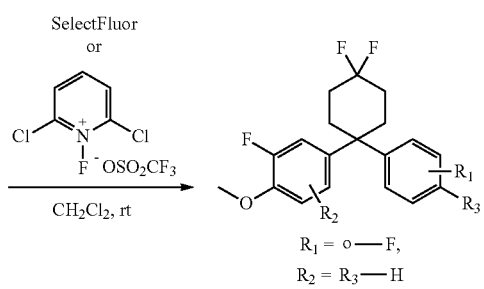

General Analytical LC-MS Procedure

Analyses were performed on a combined prep/analytical Waters/Micromass system consisting of a ZMD single quadropole mass spectrometer equipped with electro-spray ionization interface. The HPLC system consisted of a Waters 600 gradient pump with on-line degassing, a 2700 sample manager and a 996 PDA detector.

Separation was performed on an X-Terra MS C18, 5 μm 4.6×50 mm column. Buffer A: 10 mM ammonium acetate in water, buffer B: 10 mM ammonium acetate in acetonitrile/water 95/5. A gradient was run from 10% B to 100% B in 10 min, stay at 100% B for 1 min, re-equilibrate for 6 min. The system was operated at 1 mL/min.

For some analyses, separation was performed on an X-Terra MS C18, 5 μm 4.6×50 mm column. Buffer A: 10 mM ammonium acetate in water, buffer B: 10 mM ammonium acetate in acetonitrile/water 95/5. A gradient was run from 30% B to 100% B in 7 min, stay at 100% B for 1 min, re-equilibrate for 5.5 min. The system was operated at 1 mL/min.

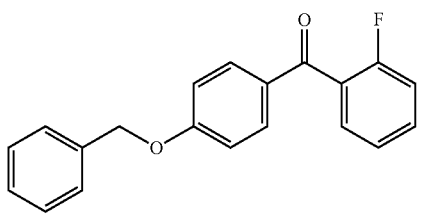

(4-(Benzyloxy)phenyl)(2-fluorophenyl)methanone
(1)

(2-Fluorophenyl)(4-hydroxyphenyl)methanone (9.0 g, 41.6 mmol), benzyl bromide (7.1 g, 41.6 mmol), and potassium carbonate (5.8 g, 41.6 mmol) were mixed in acetonitrile (60 mL). The resulting mixture was shaken at 70° C. overnight (15 h). After cooling to ambient temperature, EtOAc (200 mL) and water (100 mL) were added. The phases were separated, and the aqueous phase was further extracted with EtOAc (200 mL). The combined organic phase was washed with $Na_2CO_3$ (3×100 mL, saturated aqueous solution) and brine (100 mL), dried over $Na_2SO_4$ and filtered. Evaporation of the solvent under reduced pressure yielded 12.1 g, 95% as a slightly yellow solid. $^1$H-NMR (CDCl$_3$) δ; 7.83 (dd, 2H, J=8.8 Hz and 1.2 Hz), 7.54-7.46 (m, 2H), 7.46-7.32 (m, 5H), 7.25 (m, 1H), 7.15 (m, 1H), 7.02 (d, 2H, J=9.0 Hz), 5.14 (s, 2H); $^{13}$C-NMR (CDCl$_3$) δ 191.9, 163.1, 159.7 (d, J=251 Hz), 136.1, 132.5 (d, J=8.1 Hz), 132.3 (d, 2C, J=0.8 Hz), 130.4 (d, J=3.1 Hz), 130.4, 128.7 (2C), 128.3 (2C), 127.5, 127.5 (d, J=16.8 Hz), 124.2 (d, J=3.8 Hz), 116.1 (d, J=21.9 Hz), 114.6 (2C), 70.2.

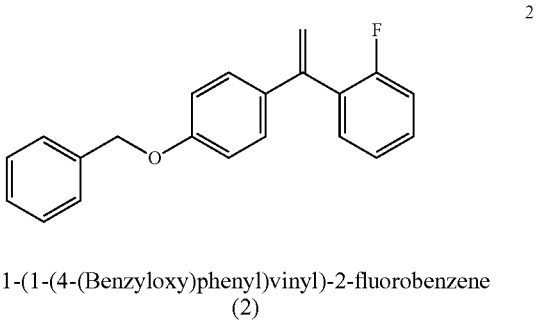

1-(1-(4-(Benzyloxy)phenyl)vinyl)-2-fluorobenzene
(2)

Compound 1 (4.0 g, 13.1 mmol) was dissolved in dry THF (40 mL) and the solution was cooled to 0° C. CH$_3$MgBr (15 mL, 19.5 mmol, 1.3 M) was added drop-wise. The resulting mixture was stirred at room temperature overnight. The solution was cooled to 0° C. and H$_2$SO$_4$ (2 mL, 98%) was added. A precipitate was formed and the inhomogeneous mixture was stirred at room temperature for 1 h. H$_2$O (20 mL) was added and the mixture was extracted with diethyl ether (2×100 mL). The organic phase was washed with NaHCO$_3$ (2×50 mL, saturated aqueous solution) and brine (50 mL) and dried over Na$_2$SO$_4$. Filtration and evaporation of the solvent under reduced pressure gave a crude material which was purified by column chromatography (heptane:ethyl acetate 6:1). Yield 2.58 g, 65% as an off-white solid. $^1$H-NMR (CDCl$_3$) δ; 7.46-7.36 (m, 4H), 7.36 (m, 5H), 7.18-7.03 (m, 2H), 6.93 (d, 2H, J=8.6 Hz), 5.68 (d, 1H, J=1.0 Hz), 5.32 (s, 1H), 5.07 (s, 2H); $^{13}$C-NMR (CDCl$_3$) δ 160.1 (d, J=248 Hz), 158.6, 143.5, 137.0, 133.4, 131.5 (d, J=3.5 Hz), 129.2 (d, J=8.1 Hz), 128.6 (2C), 128.0 (4C), 127.5 (2C), 123.9 (d, J=3.8 Hz), 115.7 (d, J=22.3 Hz), 115.3 (d, J=1.9 Hz), 114.6 (2C), 70.0.

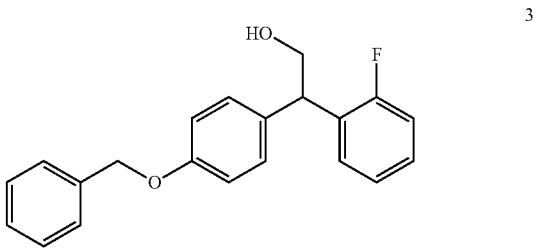 [SMILES: OCC(c1ccc(OCc2ccccc2)cc1)c1ccccc1F]

2-(4-(Benzyloxy)phenyl)-2-(2-fluorophenyl)ethanol
(3)

Compound 2 (4.01 g, 13.1 mmol) was dissolved in THF (30 mL) and the solution was cooled to 0° C. BH$_3$·THF (26.3 mL, 26.3 mmol, 1.0 M) was added drop-wise and the mixture was allowed to stir at room temperature for 3 h. The mixture was cooled to 0° C. and 10% H$_2$O in THF (8 mL), 5.6 g NaOH (dissolved in 30 mL H₂O), and 46 g H₂O₂ (35%) were sequentially added. The mixture was stirred overnight at room temperature. The mixture was acidified with aqueous HCl and extracted with diethyl ether (3×50 mL). The organic phase was washed with NaHCO₃ (50 mL, saturated aqueous solution), brine (50 mL), and dried over Na₂SO₄. Evaporation of the solvent gave 4.20 g as a crude oil. Column chromatography (heptane:ethyl acetate 4:1 to 2:1) gave 3.22 g, 76% as a semisolid. $^1$H-NMR (CDCl₃) δ; 7.46-7.26 (m, 6H), 7.25-7.18 (m, 1H), 7.21 (d, 2H, J=8.6 Hz), 7.11 (ddd, 1H, J=8.0 Hz, J=7.4 Hz and J=1.4 Hz), 7.04 (ddd, 1H, J=10.6 Hz, J=8.2 Hz and J=1.4 Hz), 6.94 (d, 2H, 8.8 Hz), 5.04 (s, 2H), 4.49 (t, 1H, 7.0 Hz), 4.15 (d, 2H, J=7.2 Hz), 1.54 (s, H₂O/OH); $^{13}$C-NMR (CDCl₃) δ 161.0 (d, J=246 Hz), 157.8, 137.0, 132.6, 129.3, 128.9 (d, J=4.6 Hz), 128.8 (d, J=14.6 Hz), 128.6, 128.3, 127.9, 127.4, 124.2 (d, J=3.8 Hz), 115.7 (d, J=22.7 Hz), 115.1, 70.0, 54.2 (d, J=1.5 Hz), 45.8 (d, J=1.9 Hz).

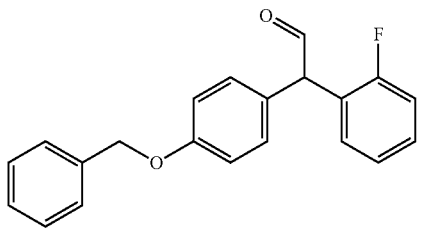

2-(4-(Benzyloxy)phenyl)-2-(2-fluorophenyl)acetaldehyde (4)

Dess-Martin periodinane (5.38 g, 12.7 mmol) was suspended in CH₂Cl₂ (70 mL). Compound 3 (3.22 g, 10.0 mmol) dissolved in 20 mL CH₂Cl₂, was added under stirring. The resulting mixture was stirred overnight at room temperature. Diethyl ether (200 mL) was added and the organic phase was washed with NaOH (2×30 mL, 2M), NaHCO₃ (50 mL, saturated aqueous solution), and brine (50 mL) and dried over Na₂SO₄. Filtration and evaporation of the solvent under reduced pressure gave a crude material which was purified by column chromatography (heptane:ethyl acetate 4:1) to yield 2.76 g, 86% of 4 as a white solid. $^1$H-NMR (CDCl₃) δ; 9.94 (dd, 1H, J=2.0 Hz and 1.5 Hz), 7.45-7.26 (m, 6H), 7.16 (d, 2H, J=8.6 Hz), 7.14-7.08 (m, 3H), 7.0 (d, 2H, J=9.0 Hz), 5.11 (ad, 1H, J=1.2 Hz), 5.07 (s, 2H); $^{13}$C-NMR (CDCl₃) δ 197.6 (d, J=1.5 Hz), 160.7 (d, J=247 Hz), 158.5, 136.8, 130.5 (d, J=2.0 Hz), 130.5 (d, J=2.0 Hz), 129.3 (d, J=8.1 Hz), 128.6, 128.0, 127.4, 127.1, 124.4 (d, J=3.5 Hz), 115.7 (d, J=22.3 Hz), 115.5 (2C), 70.1, 57.1.

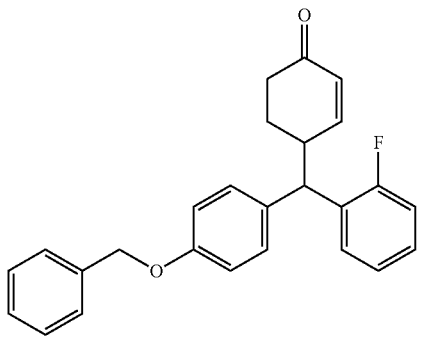

4-(4-(Benzyloxy)phenyl)-4-(2-fluorophenyl)cyclohex-2-enone (5)

A solution of KOH (110 mg, 2.0 mmol) in EtOH (3 mL) was added at 0° C. to a stirred solution of 4 (2.52 g, 7.9 mmol) and methyl vinyl ketone (0.61 g, 8.7 mmol) in THF (60 mL). The resulting mixture was stirred at room temperature overnight. Ether (200 mL) and HCl (50 mL, 10% aqueous solution) were added. The organic phase was washed with HCl (50 mL, 10% aqueous solution), H₂O (50 mL), NaHCO₃ (50 mL, saturated aqueous solution), dried over Na₂SO₄ and evaporated under reduced pressure. The crude material was dissolved in EtOH (40 mL) and HCl (2 mL, 37% aqueous solution) was added. The mixture was heated at 50° C. for 30 min under stirring. After cooling to room temperature, H₂O (50 mL) was added. The mixture was extracted with diethyl ether (3×100 mL) and the combined organic phase was washed with NaHCO₃ (2×50 mL, saturated aqueous solution) and brine (50 mL), dried over Na₂SO₄ and evaporated under reduced pressure to yield 2.89 g crude material. Purification by column chromatography (heptane:ethyl acetate 4:1 to 2:1) yielded 2.41 g, 82% as an off-white solid. $^1$H-NMR (CDCl₃) δ; 7.44-7.35 (m, 6H), 7.35-7.28 (m, 2H), 7.17 (dt, 1H, J=7.5 Hz and 1.4 Hz), 7.11 (d, 2H, J=8.9 Hz), 7.02 (dd, 1H, J=7.0 Hz and 1.4 Hz), 6.92 (d, 2H, J=8.9 Hz), 6.19 (d, 1H, J=10.3 Hz), 5.04 (s, 2H), 2.90-2.81 (m, 1H), 2.62-2.52 (m, 1H), 2.44 (at, 2H, J=6.6 Hz); $^{13}$C-NMR (CDCl₃) δ; 199.0, 161.3 (d, J=249.6 Hz), 157.9, 154.9 (d, J=3.8 Hz), 137.1 (d, J=12.1 Hz), 132.0 (d, J=10.8 Hz), 129.5 (d, J=8.8 Hz), 129.3, 128.8, 128.7 (d, J=4.2 Hz), 128.2, 128.1, 127.7, 124.3 (d, J=3.5 Hz), 117.2 (d, J=22.7), 115.0, 70.3, 47.3 (d, J=1.9 Hz), 35.1, 35.0;

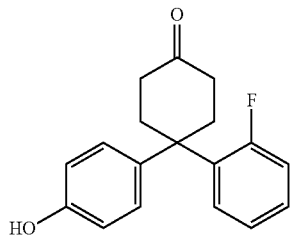

4-(2-Fluorophenyl)-4-(4-hydroxyphenyl)cyclohexanone (6)

Compound 5 (300 mg, 8.05 mmol) was dissolved in EtOAc (15 mL). Pd/C (100 mg, 10%) was added. The flask was charged with hydrogen gas (vacuum, H₂, vacuum, H₂) and the mixture was stirred overnight at room temperature. The crude mixture was filtered through a pad of celite (eluated with 40 mL of EtOAc) and the solvent was evaporated under reduced pressure to yield 230 mg, 99% of 6. $^1$H-NMR (CDCl₃) δ 7.37 (td, 1H, J=8.0 Hz and 1.7 Hz), 7.25-7.17 (m, 1H), 7.19 (d, 2H, J=8.7 Hz), 7.16-7.11 (m, 1H), 7.00-6.93 (m, 1H), 6.78 (d, 2H, J=8.2 Hz), 2.82-2.72 (m, 2H), 2.67-2.56 (m, 2H), 2.51-2.37 (m, 4H), 1.43 (s, H₂O/OH); $^{13}$C-NMR (CDCl₃) δ 211.9, 161.4 (d, J=248 Hz), 154.2, 136.7, 132.9 (d, J=10.8 Hz), 128.7 (d, J=8.8 Hz), 128.3 (d, J=5.0 Hz), 127.9 (d, 2C, J=1.1 Hz), 124.1 (d, J=3.5 Hz), 117.0 (d, J=24.2 Hz), 115.3 (2C), 44.2 (d, J=2.7 Hz), 38.5 (2C), 35.5 (d, 2C, J=4.6 Hz); $^{19}$F-NMR (CDCl₃) δ−108.6 (m).

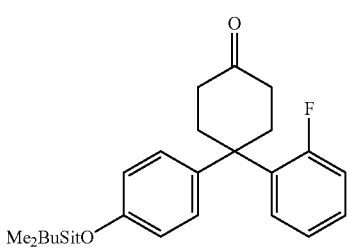

4-(4-(Tert-butyldimethylsilyloxy)phenyl)-4-(2-fluorophenyl)cyclohexanone (7)

Imidazole (128 mg, 1.9 mmol) was added to a solution of 6 (214 mg, 0.75 mmol) and TBDMSCl (136 mg, 0.90 mmol) in DMF (8 mL). The mixture was stirred at room temperature overnight. NaHCO$_3$ (10 mL, saturated aqueous solution) was added and the mixture was extracted with EtOAc (2×40 mL). The combined organic phase was dried over Na$_2$SO$_4$ and the solvent was evaporated under reduced pressure. The concentrate was dissolved in EtOAc (50 mL) and the solution was washed with MgSO$_4$ (4% aqueous solution). The organic phase was dried over Na$_2$SO$_4$, filtered and the solvent was evaporated under reduced pressure. Yield of crude: 394 mg (>100%) as a thick oil.

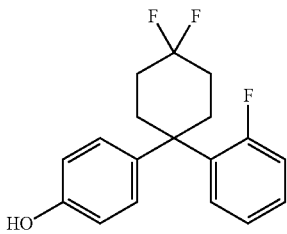

4-(4,4-Difluoro-1-(2-fluorophenyl)cyclohexyl)phenol (8)

Deoxofluor (222 mg, 1.0 mmol) was added to a solution of 7 (100 mg, 0.25 mmol) in CH$_2$Cl$_2$ (2 mL). The resulting solution was stirred at room temperature overnight followed by careful addition of MeOH (1 mL). EtOAc (20 mL) was added and the organic solution was washed with NaHCO$_3$ (2×5 mL, saturated aqueous solution) and dried over Na$_2$SO$_4$. Filtration followed by evaporation of the solvent under reduced pressure gave a crude semisolid. Purification by combi-flash chromatography (heptane-ethyl acetate 5-25%, then heptane-ethyl acetate 5-12%) yielded 30 mg of 8 as a semisolid. $^1$H-NMR (CDCl$_3$) δ 7.32 (td, 1H, J=8.0 Hz and J=1.8 Hz), 7.24-7.17 (m, 1H), 7.17-7.08 (m, 1H), 7.14 (d, 2H, J=8.9 Hz), 6.93 (ddd, 1H, J=12.8 Hz, 8.1 Hz and 1.4 Hz), 6.74 (d, 2H, J=8.6 Hz), 2.64-2.52 (m, 2H), 2.50-2.39 (m, 2H), 2.09-1.87 (m, 4H).

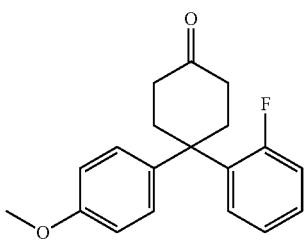

4-(2-Fluorophenyl)-4-(4-methoxyphenyl)cyclohexanone (100)

Compound 6 (678 mg, 2.38 mmol) and K$_2$CO$_3$ (91 mg, 2.38 mg) were mixed in acetone (20 mL). MeI (406 mg, 2.86 mmol) was added and the mixture was heated at reflux overnight. Aqueous work-up and column chromatography (heptane:EtOAc 4:1 to elution with pure EtOAc) gave 270 mg of 10 and 360 mg of recovered 6.

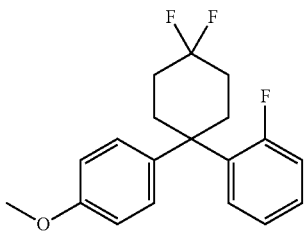

1-(4,4-Difluoro-1-(4-methoxyphenyl)cyclohexyl)-2-fluorobenzene (9)

Compound 100 (270 mg, 0.91 mmol) was dissolved in CH$_2$Cl$_2$ (5 mL). DAST (266 µL, 2.0 mmol) was added followed by methanol (4 µL). The mixture was stirred at room temperature overnight. Na$_2$S$_2$O$_3$ (10%, 2 mL) was added and the mixture was extracted with EtOAc (2×30 mL). The combined organic phase was washed with NaHCO$_3$ (20 mL, saturated aqueous solution), brine (20 mL) and dried over Na$_2$SO$_4$. Filtration and evaporation of the solvent under reduced pressure gave a crude material which was purified by column chromatography (heptane:EtOAc 6:1) to give 185 mg of a mixture of 9 and the corresponding vinyl fluoride. This mixture was exposed to NMO (35 mg, 0.30 mmol) and OsO$_4$ (15 µL, 2.5% solution in $^t$BuOH) in acetone:water mixture (8:1, 2 mL) to aid purification of the desired compound. The mixture was stirred overnight. Aqueous work-up followed by column chromatography (pentane:CH$_2$Cl$_2$ 90:10) gave 90 mg of 9. $^1$H-NMR (CDCl$_3$) δ 7.34 (td, 1H, J=4.3 Hz and 1.8 Hz), 7.24-7.18 (m, 1H), 7.21 (dd, 2H, J=9.2 Hz and 1.0 Hz), 7.15-7.08 (m, 1H), 6.94 (ddd, 1H, J=13.0 Hz, 8.2 Hz and 1.4), 6.83 (d, 2H, J=9.0 Hz), 3.78 (s, 3H), 2.66-2.56 (m, 2H), 2.52-2.42 (m, 2H), 2.07-1.87 (m, 4H); $^{13}$C-NMR (CDCl$_3$) δ 161.5 (d, J=248 Hz), 157.8, 136.9, 133.0 (d, J=10.4 Hz), 128.5 (d, J=9.2 Hz), 128.3 (J=5.0 Hz), 127.8 (d, J=1.1 Hz), 124.0 (d, J=3.5 Hz), 123.2 (at, J=242 Hz), 117.0 (d, J=24.2 Hz), 113.7, 55.1, 43.9 (d, J=2.7 Hz), 32.2 (dd, J=10.8 Hz and J=5.0 Hz), 31.2 (at, J=24.0 Hz); $^{19}$F-NMR (CDCl$_3$) δ −108.5 (m), −96.1 (bs, 2F).

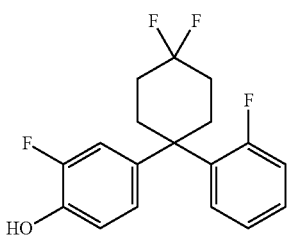

4-(4,4-Difluoro-1-(2-fluorophenyl)cyclohexyl)-2-fluorophenol (10)

A mixture of 8 and the corresponding vinyl fluoride (220 mg, 0.70 mmol) was dissolved in CH$_2$Cl$_2$ (4 mL). 2,6-di- Chloro-N-fluoropyridinium triflate (227 mg, 0.72 mmol) was added and the mixture was stirred at room temperature overnight. Evaporation of the solvent followed by combiflash purification (heptane-ethyl acetate 2-20%) gave 24 mg of 10. $^1$H-NMR (CDCl$_3$) δ 7.35 (td, 1H, J=8.2 Hz and 1.8 Hz), 7.26-7.20 (m, 1H), 7.14 (td, 1H, J=7.6 Hz and 1.4 Hz), 7.02-6.88 (m, 4H), 5.08 (bs, 1H, —OH), 2.63-2.54 (m, 2H), 2.45-2.35 (m, 2H), 2.09-1.87 (m, 4H); $^{13}$C-NMR (CDCl$_3$) δ 161.4 (d, $J_{C,F}$=249 Hz), 150.7 (d, $J_{C,F}$=237 Hz), 141.6 (d, $J_{C,F}$=14.2 Hz), 138.4 (d, $J_{C,F}$=5.0 Hz), 132.2 (d, $J_{C,F}$=10.4 Hz), 128.8 (d, $J_{C,F}$=9.2 Hz), 128.2 (d, $J_{C,F}$=5.0 Hz), 124.1 (d, $J_{C,F}$=3.1 Hz), 123.0 (dd, $^1J_{C,F}$=237 Hz and 243 Hz), 123.0 (d, $J_{C,F}$=4.6 Hz), 117.1 (d, $J_{C,F}$=24.2 Hz), 116.9 (d, $J_{C,F}$=2.3 Hz), 114.2 (d, $J_{C,F}$=19.2 Hz), 43.9, 32.3 (dd, $J_{C,F}$=10.8 Hz and 4.6 Hz), 31.1 (at, $J_{C,F}$=24.0 Hz). $^{19}$F-NMR (CDCl$_3$) δ −140.4, −108.5, −96.9 (d, $J_{F,F}$=238.2), −95.8 (d, $J_{F,F}$=234.8).

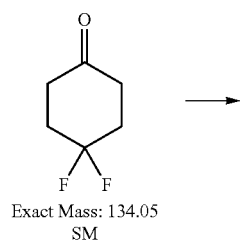

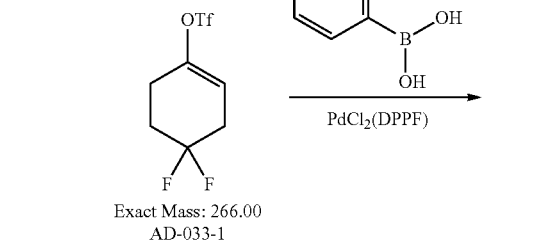

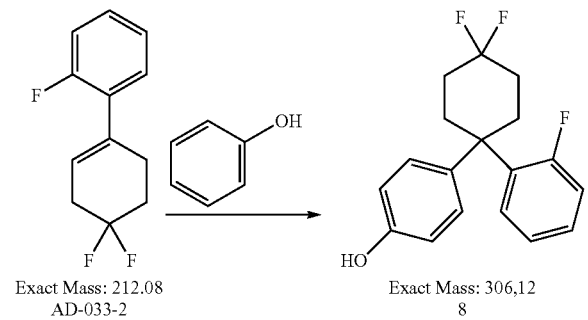

Step 1:

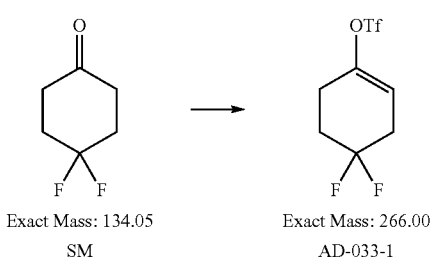 [SMILES: O=C1CCC(F)(F)CC1 ; O=S(=O)(OC1=CCC(F)(F)CC1)C(F)(F)F]

To a solution of n-butyl lithium 1.6M (1.5 eq) in hexane and THF at −78° C. under N$_2$, was added drop-wise fresh purified HN (i-Pr)$_2$ (1.2 eq). After stirring during 30 min, a solution of 4,4-difluorocyclohexanone (30 g, 0.224 mol, 1 eq)/DME was added. After stirring during 15 min the enolate solution was warmed to room temperature and stirred for 2 h. It was then cooled to −78° C. and a solution of N-phenyl-triflinide (1.3 eq, 0.291 mol)/DME was added to the enolate at −78° C. The reaction mixture was warmed to 0° C. and stirred overnight. The resulting solution was poured into water, the volume was reduced under vacuum and the residue was taken up with ethyl acetate was washed with water. The organic phase was dried over Na$_2$SO$_4$, the solids were filtered and the solvent evaporated. The compound denoted AD033-1 in the schemes was obtained and used directly.

Step 2:

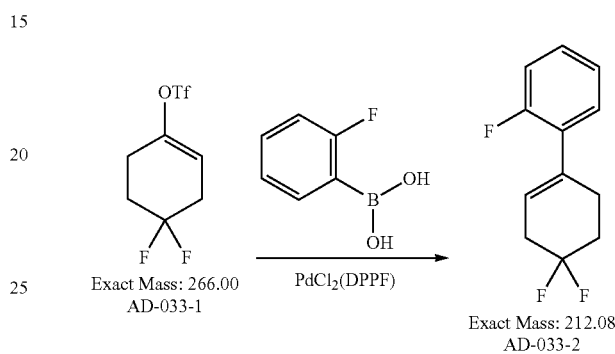

A mixture of crude the compound denoted AD033-1,2-fluorobenzeneboronic acid (0.246 mol, 1.1 eq to 4,4-difluorocyclohexanone), KF.2H$_2$O (0.672 mol, 3 eq) and PdCl$_2$(DPPF) (0.0246 mol, 0.1 eq) in DMF stirred at room temperature overnight. When the reaction was complete, it was poured into water, and was EA (ethyl acetate) extracted and then the organic phase was filtered through celite, rinsed with EA, which was washed with brine and concentrated to subject silica gel chromatography that give 17 g of the compound denoted AD-033-2 in the schemes. Total yield of two steps is 35%.

Step 3:

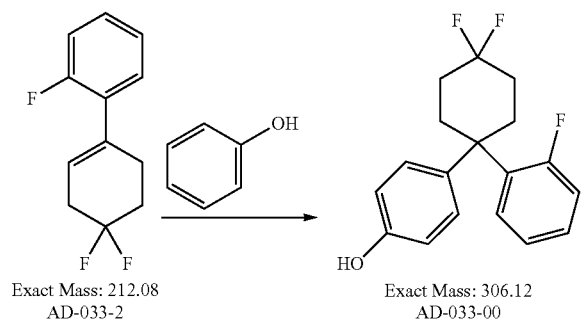

The compound denoted AD033-2 (17 g, 80 mmol), phenol (2.5 eq, 200 mmol) and BF$_3$H$_3$PO$_4$ (catalytic amount) were mixed and shaken at room temperature overnight. CH$_2$Cl$_2$ was added and the organic phase was washed with saturated NaHCO$_3$ several times, then washed with hot saturated aqueous potassium carbonate solution to remove most of the phenol, washed with brine, dried with Na$_2$SO$_4$, concentrated and purified through column chromatography (eluent with EA/PE=1:50; PE being petroleum ether) three times, and then recrystallization to give compound 8 (11.2 g). Yield 45%. Mp: 83-85° C.

Please note that in the synthesis above the amount of the compound denoted AD033-2 should be more then several grams so it can be used as solvent. Furthermore, phenol cannot be removed completely by hot saturated aqueous potassium carbonate solution so careful column chromatography is needed (eluent with EA/PE=1:50). After column purification, there is a small point on TLC closely to the point of desired product which could be monitored by three times of TLC in EA/PE=1:4 system, so recrystallization form EA/Et2O/DCM/PE=1:1:1:15 is necessary to make sure the purity is >97%.

Experimental Description Of Biochemical Assays

R-SAT® assays

R-SAT® (Receptor Selection and Amplification Technology) is a cell-based functional assay that allows one to monitor receptor-dependent proliferative responses and has been described elsewhere. The technology has been validated for a number of receptors including GPCRs (Bräuner-Osborne H, Brann M R., Eur J. Pharmacol. 1996 Jan. 4; 295(1):93-102), RTKs (Burstein E. S., Hesterberg D. J., Gutkind J. S., Brann M. R., Currier E. A. and Messier T. L., Oncogene (1998) 17, 1617-1623), cytokine receptors (Piu F., Magnani M. and Ader M. E., Oncogene (2002) 21:3579-91) and nuclear receptors (Piu F., Gauthier N. K., Olsson R., Currier E. A., Lund B. W., Croston G. E., Hacksell U. and Brann M. R., Biochem Pharmacol. (2005) 71:156-62; Piu F., Gauthier N. K. and Wang F., Oncogene (2006) 25:218-29). This process is achieved by partial cellular transformation via loss of contact inhibition and growth factor dependency. Monitoring is achieved by transfecting the cells with a β-galactosidase reporter gene vector whose expression is under a constitutively active promoter. Briefly, NIH-3T3 fibroblasts were plated overnight in 96-wells plates in DMEM 10% calf serum (Hyclone) and grown to 60-70% confluency prior to transfection. Transient transfections were performed using Polyfect (Qiagen) according to manufacturer's instructions. Typically a transfection mix would consist of the receptor and the β-galactosidase expression vectors. Sixteen hours post-transfection, cells were incubated with different doses of ligand in DMEM containing 30% Ultraculture (Hyclone) and 0.4% calf serum (Hyclone) to generate a dose response curve. After 5 days, plates were developed by adding onto the washed cells a solution containing the β-galactosidase substrate o-nitrophenyl-D-galacto pyranoside ONPG (in phosphate-buffered saline with 5% Nonidet P-40 detergent) as described (Piu F., Magnani M. and Ader M. E., Oncogene (2002) 21:3579-91).

Plates were read using a microplate reader at 420 nm. Data from R-SAT® assays were fit to the equation: $r = A + B(x/(x+c))$, where A=minimum response, B=maximum response minus minimum response, $c=EC_{50}$, r=response, and x=concentration of ligand. Curves were generated using the curve fitting softwares Excel Fit and GraphPad Prism (San Diego, Calif.). The results are shown in Table 1.

Luciferase Reporter Gene Assay

HEK293 cells were grown to 70% confluency in DMEM containing 10% calf serum (Hyclone) prior to transfection. On the day of transfection (day 1), expression vectors for ERα or ERβ were cotransfected along a construct containing a synthetic 3*ERE upstream of the luciferase gene (Panomics), using Polyfect (Qiagen) per manufacturer's recommendations (ERE being estrogen response element). Sixteen hours post-transfection, cells were incubated in serum free DMEM. On day 3, cells were incubated with the test compounds for 48 hours in serum free DMEM. Cells extracts were then obtained by lyzing and the Luciferase activity measured, all of these steps performed using a commercially available kit (Promega). The results are shown in Table 1.

Binding Assay

HEK293T cells were transiently transfected for 48 hours with expression vectors encoding ERα or ERβ, before being serum starved for 4-6 hours. Cells were then harvested by scraping in ice-cold PBS and subsequently lysed using a cold buffer containing 10 mM Tris pH 7.4, 1 mM EDTA, 1 mM DTT before being subjected to polytron twice for 10 seconds. Cytosolic extracts were isolated by centrifugation at 15000 g for 30 minutes at 4° C. Competitive binding of the test compounds or the estradiol control was performed on 20 μL extract by overnight incubation at 4° C. in a total volume of 100 μL containing 1 nM $^3$H-estradiol (Perkin Elmer, Boston, Mass.). The bound fraction was separated from the unbound one by the addition of 100 μL of Dextran coated charcoal, incubated for 10 minutes and subsequent centrifugation at 1000 rpm for 10 minutes. Samples (100 μL per sample) were then analyzed by liquid scintillation. Data was then analyzed using the curve fitting software GraphPad Prism. The results are shown in Table 1.

Metabolic Stability

Also the metabolic stability in liver microsomes was tested for some compounds. A low value for the metabolic stability indicates that the compound is metabolicly stable. The results are shown in Table 1.

TABLE 1

Results for the biochemical assay

| | R-SAT | | | | Luciferase | | | | Binding | | Metabolic stability | |
|---|---|---|---|---|---|---|---|---|---|---|---|---|
| | Erα | | Erβ | | Erα | | Erβ | | ERα | ERβ | $Cl_{int}$ (μL/(min mg)) | |
| Comp. | % | | % | | % | | % | | | | | |
| No. | Eff | $pEC_{50}$ | Eff | $pEC_{50}$ | Eff | $pEC_{50}$ | Eff | $pEC_{50}$ | pKi | pKi | Human | Rat |
| 8 | 62 | 6.0 | 69 | 8.9 | 32 | 6.2 | 96 | 9.2 | 7.1 | 8.2 | 11 | 150 |
| 10 | 100 | 6.0 | 57 | 8.6 | 2 | na | 55 | 8.7 | 6.6 | 8.3 | 11 | 95 |
| 12 | 74 | na | 42 | 8.5 | 30 | na | 74 | 9.2 | 7.0 | 8.4 | 0 | 147 |
| 14 | 145 | 7.0 | 60 | 8.8 | 82 | na | 52 | 9.2 | 7.3 | 8.4 | 0 | 113 |
| 957 * | 58 | 6.2 | 94 | 8.8 | 13 | na | 62 | 8.9 | 6.7 | 7.8 | 20 | 450 |
| 623 * | 45 | 6.4 | 89 | 8.2 | 15 | 6.4 | 99 | 8.3 | 6.1 | 8.2 | | |
| 152 * | 29 | 5.8 | 69 | 7.9 | 48 | 5.4 | 126 | 7.7 | | 7.2 | 27 | 405 |
| 131 * | 42 | 5.5 | 71 | 7.5 | 29 | 4.8 | 80 | 7.7 | 6.0 | 7.3 | | |
| 558 * | 48 | 5.9 | 73 | 8.2 | 37 | 5.8 | 101 | 8.6 | 6.0 | 7.3 | | | na = not active
* = comparative substance; 131 and 558 are compounds disclosed in WO 2007/056500

TABLE 1-continued

Results for the biochemical assay

| | R-SAT | | | | Luciferase | | | | | | Metabolic stability | |
|---|---|---|---|---|---|---|---|---|---|---|---|---|
| | Erα | | Erβ | | Erα | | Erβ | | Binding | | $Cl_{int}(\mu L/(min\cdot mg))$ | |
| Comp. No. | % Eff | $pEC_{50}$ | % Eff | $pEC_{50}$ | % Eff | $pEC_{50}$ | % Eff | $pEC_{50}$ | ERα pKi | ERβ pKi | Human | Rat |

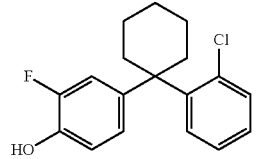

957

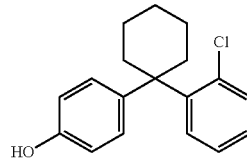

623

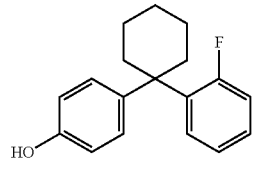

152

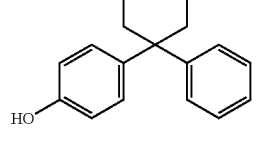

131

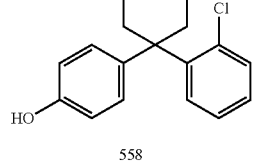

558

TABLE 2

Results for the Microsomal bioavailability

| Comp. No. | F (%) |
|---|---|
| 8 | 4.2 |
| 9 | 19.6 |
| 131 * | 0 |
| 558 * | 2 |

* = comparative substance

Determination of the Bioavailability of Compound 8 Following Intravenous and Sublingual Administration in Male Beagle Dogs In this example, the sublingual bioavailability of Compound 8 was evaluated after intravenous and sublingual doses in male beagle dogs. The test compound was dosed at 1 and 10 mg/kg through intravenous and sublingual routes, respectively. Plasma samples were collected 10 min, 20 min, 30 min, 45 min, 1 hour, 2 hours, 4 hours, 8 hours, 12 hours and 24 hours post dose. Plasma levels were determined by LC-MS/MS analysis. A pre-study standard curve was analyzed to determine the specificity, range and lower limit of quantification of the LC-MS/MS method. The study samples were treated identically to the standards. Pharmacokinetic parameters were estimated by a non-compartmental model using WinNonlin v4.1 software.

Following intravenous dosing at 1 mg/kg, average maximum concentration ($C_{max}$) was 738±199 ng/mL. The average clearance and volume of distribution were 2.82±0.78 L/hr/kg and 3.5±0.9 L/Kg, respectively. $C_{max}$ increased 2-fold, while the clearance and volume of distribution decreased 2-fold compared to those parameters observed in rats. After sublingual dosing at 10 mg/kg, the average half-life was found to be 2.08±0.50 hours and $C_{max}$ (1064±110 ng/mL) reached between 20 and 60 minutes. The overall percent bioavailability of Compound 8 following sublingual dose found to be 44%±12.

Determination of the Bioavailability of Compounds 8 and 9 Following Intravenous and Sublingual Administration in Rat Similarly to the Example above, Compound 8 was also administered to rat intravenously, orally and sublingual. Also the prodrug of Compound 8, i.e. Compound 9, was administered. The results are shown in FIG. 1. The bioavailability (% F) indicated for the prodrug Compound 9 is the results of measurements of the bioavailability for Compound 8, which Compound 9 is converted into upon administration. AUC 0-4 was used for calculation of the bioavailability.

Unidirectional Permeability of Compound 8 Compared to Comparative Substance 623 and Comparative Substance 957 Across MatTek EpiOral Buccal Tissue Based on the apparent permeability coefficients ($P_{app}$) of the test compounds assessed in MatTek EpiOral buccal tissue, it is shown that Compound 8 can be classified as a highly permeable compound, like caffeine; while the comparative substances 623 and 957 can be classified as having low permeability, similar to atenolol.

Control compounds, atenolol and caffeine, were purchased from SigmaAldrich (St. Louis, Mo., USA). EpiOral→tissues plated in 24-well plates were obtained from MatTek Corporation (Ashland, Mass., USA). The assay buffer was Dulbeccos' Phosphate Buffered Saline (DPBS) without Ca & Mg chloride, pH 7.4.

Non-specific binding assessment (NSB) was conducted in a tissue-free plate containing Millipore Millicell culture plate inserts that were the same ones that were used in the permeation study across the culture tissues. Each of the tested compounds was dosed at 1 µM with DPBS buffer. Sampling time for the receiver chambers was 120 minutes after dosing, while the donor sides were sampled at 0 and 120 minutes after dosing. The NSB assessments consisted of the permeation rates across tissue-free inserts and the percent recovery by calculating the mass balance of the test campounds at the end of the experiment. The recovery assessment was used to assess the non-specific binding property of the tested compounds to the assay apparatus.

Each test compound was co-dosed with the two control compounds. Targeting dosing concentrations were 10 µM for each test compound and 100 µM for the two control compounds. Prior to the permeability assay onset, the tissues were preequilibrated in a pre-warmed EpiOral assay medium for one hour at 37° C. in a 5% $CO_2$ incubator. The EpiOral assay medium was aspirated after the pre-equilibration, and the tissues were washed twice with the DPBS buffer. The receiver chambers were filled with 0.75 mL of the DPBS buffer, while the donor chambers received 0.4 mL of the dosing solutions. The assay plates were placed at 37° C. in a 5% $CO_2$ incubator. The receiver samples (200 µL) were collected at 30, 60, and 120 minutes, and replaced with an equal volume of fresh pre-warmed receiver buffer (except for the last time point of 120 minutes). The donor sides were sampled at 0 and 120 minutes. The test compounds were then analyzed using LC-MS/MS.

The apparent permeability coefficient, $P_{app}$, and recovery rate were calculated as follows:

$$P_{app}=(dC_r/dt) \times V_r/(A \times C_{ini})$$

Recovery rate (%)=[((Cr, final·Vr)+(Cd, final·Vd))/(Cn·Vd)]·100 wherein:
dCr/dt is the slope of cumulative concentration in the receiver compartment over time in µM/min;
$V_r$ is the volume of the receiver compartment;
$V_d$ is the volume of the donor compartment;
A is the diffusional area of the membrane;
$C_{ini}$ is the initial donor concentration in µM;
$C_{D, final}$ is the donor concentration at 120 minute in µM;
$C_{r, final}$ is the receiver concentration at 120 minute in µM;
$C_n$ is the nominal concentration in µM.

Both comparative substances, 623 and 957, had low recovery (22% and 18%, see Table 1) and low apparent permeability coefficients ($P_{app}$) ($1.17\times10^{-6}$ cm/s and $0.881\times10^{-6}$ cm/s), suggesting that the two comparative substances had a tendency to heavily stick to the test device and exhibited slow diffusion rates through the cell-free insert.

Compound 8 passed through the cell-free insert with a $P_{app}$ value of $19.8\times10^{-6}$ cm/s, with a moderate recovery of 57%. The results indicated that Compound 8 could freely diffuse through the insert, but also had a tendency to stick to the test apparatus (<80% recovery).

Then unidirectional permeation assessment for the TCs across the MatTek buccal tissues was conducted in parallel with the two control compounds.

Apparent permeability coefficient of comparative compound 623 was $3.08\times10^{-6}$ cm/s, while the control compounds in the same group exhibited distinct permeation characteristics, in which atenolol had a $P_{app}$ value at $1.95\times10^{-6}$ cm/s, and caffeine passed through the tissues at a rate of $23.1\times10^{-6}$ cm/s. With such distinct observations (low vs. high permeability), it was all but certain that the tissues properly functioned as expected. Comparative compound 623 can be classified as having a low permeability across the MatTek OpiOral buccal tissues. It should be pointed that the permeability of Comparative compound 623 might be underestimated because of its low recovery that might be the result of (1) the compound sticking to the test device with only 22% recovery in the non-specific binding assay, and (2) a moderate amount of compound still being trapped in the tissues by the end of the incubation period.

Apparent permeability coefficient of Comparative compound 957 was $3.91\times10^{-6}$ cm/s, while the control compounds in the same tissues exhibited distinct permeation characteristics, in which atenolol had a $P_{app}$ value at $1.57\times10^{-6}$ cm/s, and caffeine passed through the tissues at a rate of $27.5\times10^{-6}$ cm/s. Thus, it was evident that the tissues properly functioned. Like atenolol, Comparative compound 957 can be classified as having a low permeability across the MatTek OpiOral buccal tissues. It should be noted that the permeability of Comparative compound 957 might be underestimated because of its low recovery, which resulted from (1) the compound having a tendency to stick to the test device as only 18% recovery was found in the non-specific binding assay, and (2) quite an amount of compound was still trapped in the tissues by the end of the incubation period.

Apparent permeability coefficient of Compound 8 was $12.5\times10^{-6}$ cm/s, while the control compounds in the same tissues exhibited distinct permeation characteristics, in which atenolol had a $P_{app}$ value of $1.73\times10^{-6}$ cm/s, and caffeine passed through the tissues at a rate of $22.3\times10^{-6}$ cm/s. The permeability coefficient of Compound 8 was closer to that of caffeine than that of atenolol; it can be classified as to have a high permeability across the MatTek OpiOral buccal tissues. It should be also pointed that the permeability of Compound 8 might be underestimated because of its low recovery, which mainly resulted from (1) a moderate amount of compound being trapped in the tissues by the end of the incubation period, and (2) the compound having a tendency to stick to the test device with 57% recovery in the non-specific binding assay.

Treatment of Parkinson's Disease with Compound 8

Summary

Bilateral 6-hydroxydopamine (6OHDA) lesion of the substantia nigra (SN) was employed to assess the neuroprotective effects of ERβ agonists. Compound 8 and the three Comparative substances, 131, 623 and 957, which all are selective ERβ agonists, were compared with estradiol for their ability to prevent the behavioral and neurochemical effects of 6OHDA infusion. Male rats were selected as subjects since any viable treatment for Parkinson's disease (PD) must work for both women and men, and most of the studies found in the literature were focusing on females suggesting that the demonstration of ER effects is more difficult in male animals. Estradiol, Compound 8 and the three Comparative substances, 131, 623 and 957 were assessed for their ability to prevent deficits induced by 6OHDA lesions. The ERβ agonists were able to prevent motor, cognitive and sensorimotor gating deficits associated with 6OHDA lesion of the SN and to mitigate the loss of dopamine neurons in the SN. Interestingly, estradiol did not show the same neuroprotective benefits as the selective ERβ agonists. This is consistent with a recent publication that reviewed sex-specific neuroprotection by estrogens, where it was concluded that while administration of exogenous estradiol to females has a protective effect against DA loss, administration of exogenous estradiol in males has negligible or even harmful effects. In addition, recently it was found that a metabolite of testosterone, 5α-androstane-3β, 17β,-diol, selectively activate the ERβ-receptor. Interestingly, this metabolite is formed via the DHT route which is distinguished from the route giving estradiol from testroterone.

Compounds in this class has shown activity in the CFA model of chronic inflammatory pain using oral dosing, with a higher dose (30 mg/kg) compared especially due to first pass phase II transformations, this corroborated with in vitro data from human, rat and dog hepatocytes in human and rat hepatocytes all compounds had a half-life of approximately 15 min. While liver rat and dog microsomes were equally effective as the hepatocytes of clearing the compounds, this class of compounds was stable in human liver microsomes. Two approaches have been taken to overcome the difficulty: the use of prodrugs that limit first pass metabolism and the use of alternate routes of administration. Both approaches have proven fruitful. Three of our selective ERβ agonists were assessed for their permeability across human buccal membranes. Based on the apparent permeability coefficients ($P_{app}$) of the test compounds assessed in MatTek EpiOral buccal tissue, it was concluded that Compound 8 can be classified as a highly permeable compound, like caffeine; while Comparative substances 623 and 957 can be classified as to have low permeability, similar to atenolol, as discussed above. It was found that Compound 8 was highly permeable across these membranes and therefore selected as a good candidate for further PK studies via the buccal/sublingual administration. In rats Compound 8 showed around 8% oral bioavailability. Compound 8 assessed following sublingual administration in rats showed 79%. Furthermore, the sublingual bioavailability of Compound 8 was evaluated after intravenous and sublingual doses in male beagle dogs, Compound 8 showed 44% bioavailability and 2 h half life, as discussed above. These results are based on using an unoptimized vehicle, selected mainly due to the fact that it solubilizes the compound. The first prodrug of Compound 8 that was synthesized, i.e. Compound 9, had an increased oral bioavailability 20% compared to the 8% and given sublingual in rat it gave an 85% bioavailability of Compound 8. Thus, the uses of prodrugs, buccal administration, or both, have proven viable means of improving bioavailability and moving this class of compounds towards clinical use.

6OHDA Model Data:

Male rats received baseline assessment of weight, motor function (spontaneous locomotor behavior, rotorod performance) and sensorimotor gating (prepulse inhibition). Subjects were assigned to treatment conditions to equalize performance on all these measures. Subjects were then treated once daily for 7 days with either sesame oil vehicle, estradiol (100 μg/kg sc), Comparative substance 131 (10 mg/kg sc), Compound 8 (10 mg/kg sc), Comparative substance 623 (10 mg/kg sc) or Comparative substance 957 (10 mg/kg sc). On the second day of treatment, subjects received bilateral sham or 6OHDA lesions (8 μg in 4 μl) of the substantia nigra (A/P−5.0 mm, M/L±1.6 mm, D/V−8.2 mm) following the atlas of Paxinos and Watson (Paxinos, G., Watson, C., The Rat Brain in Stereotaxic Coordinates, Fourth Edition, New York: Academic Press, Spiral Bound, 1998). Behavioral assessments of motor function (spontaneous locomotion, rotorod and traversing a challenging beam), cognition (novel object recognition) and sensorimotor gating (prepulse inhibition) began after the final day of treatment. Following behavioral assessment, SN and striatal tissue were collected in order to determine the intactness of the nigrostriatal dopamine system.

Figure 2:
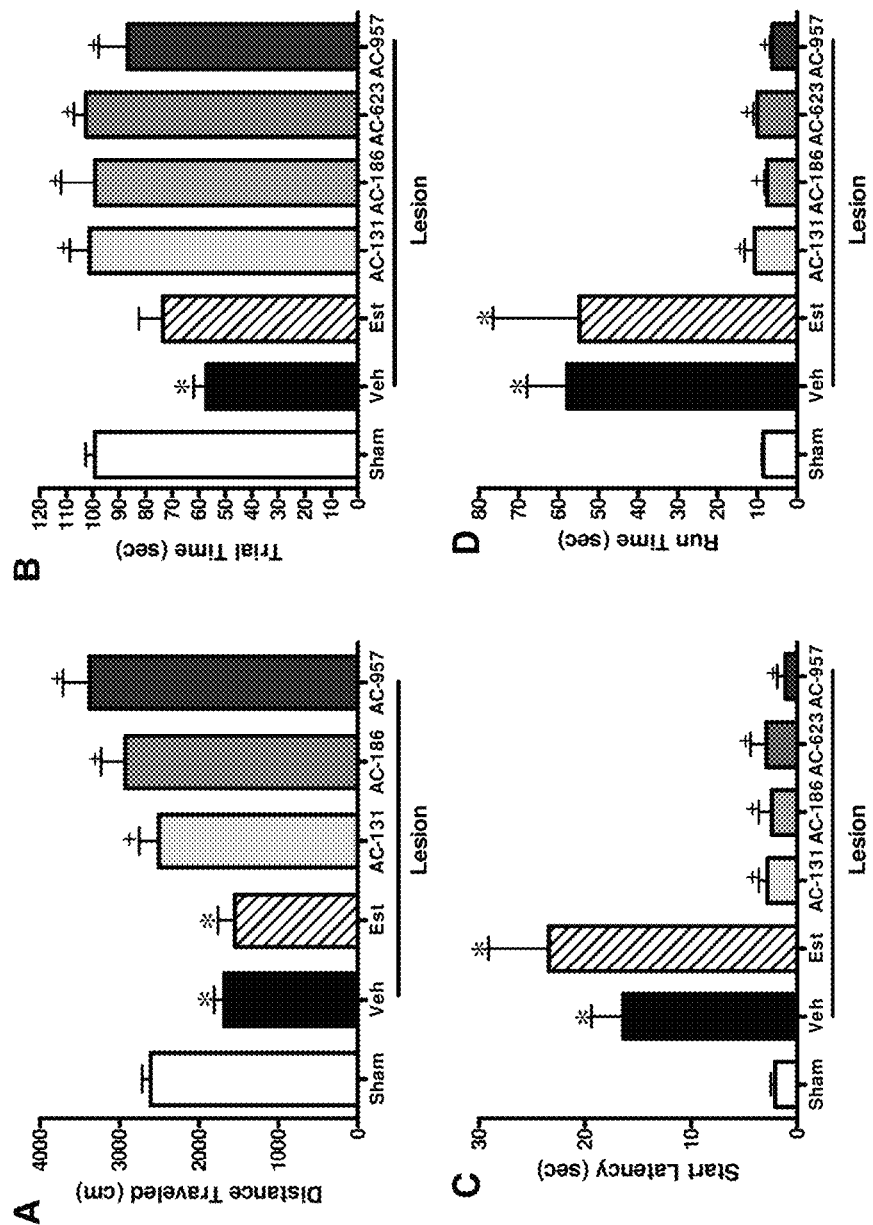
FIG. 2 displays the motor performance of sham (all treatments combined) and 6-hydroxydopamine animals treated with sesame oil vehicle (Veh), estradiol (Est), Comparative substance 131 (AC-131), Compound 8 (AC-186), Comparative substance 623 (AC-623) or Comparative substance 957 (AC-957). Panel A shows distance traveled during a 15 min spontaneous locomotor session. Panel B shows the time animals remained on the rotorod on the test trials. Panels C and D show the start latency and time required to traverse the challenging beam, respectively. For each of these measures of motoric ability, 6OHDA treatment impaired performance, and treatment with an ERβ agonist (AC-131, AC-186, AC-623 or AC-957) prevented the impairment. Data were analyzed using one-way ANOVAs, followed by Bonferroni's multiple comparison post hoc analyses. * indicates a significant difference from sham treated animals, p<0.05. + indicates a significant difference from vehicle/6OHDA, p<0.05.

In all cases, sham animals treated with vehicle, estradiol, Comparative compound 131, Compound 8, Comparative compound 623 or Comparative compound 957 displayed no behavioral differences. Thus, for clarity, data from sham animals were pooled. Relative to sham controls, lesioned animals (6OHDA/vehicle) displayed impaired motor performance (FIG. 2) as measured by spontaneous locomotor activity, the ability to remain on a rotorod that gradually increased speed of rotation, or the ability to traverse a challenging beam. Lesioned animals also showed impaired cognition (FIG. 3) and sensorimotor gating (FIG. 4), deficits that are commonly observed in Parkinson's patients. Treatment with Comparative compound 131, Compound 8, Comparative compound 623 or Comparative 957 beginning one day prior to 6OHDA infusion prevented the expression of all of these behavioral deficits, with the exception that Comparative compound 957 did not reverse the cognitive deficit associated with SN lesions. Notably, treatment with estradiol did not reliably improve motor or cognitive performance, although it did have equal ability to prevent deficits in prepulse inhibition. Comparative compound 131 and Compound 8 were compared with estradiol for their ability to protect nigrostriatal dopamine neurons as measured by tyrosine hydroxylase (TH) immunohistochemistry in the SN and striatum (STR). Consistent with an improved behavioral profile, animals that received Comparative compound 131 or Compound 8 showed an improved profile of tyrosine hydroxylase immunofluorescence in the SN (FIG. 5) and STR (FIG. 6). Estradiol, Comparative compound 131, or Compound 8 treatment resulted in an increased number if tyrosine hydroxylase positive cells in the SN compared with vehicle treated animals. Further, in animals treated with the selective ERβ agonists Comparative compound or Compound 8, but not in animals treated with estradiol, the size of the immunopositive cells (pixels/cell), the percent of the image that was immunopositive (probably reflecting both cell size and presence of large, visible fibers), and the intensity of immuno fluorescence (reflecting TH density) was improved relative to vehicle-treated animals. Similarly, selective activation of ERβ receptors with Comparative compound 131 or Compound 8, but not nonselective activation with estradiol, was able to protect dopaminergic terminals in the STR as reflected by percent of the image that was immunopositive and the intensity of TH immunofluorescence. Thus, the selective agonists Comparative compound 131 and Compound 8 were better able to protect the viability or functionality of dopamine cells in the SN and STR compared with estradiol, and this fact is reflected in a normalized behavioral profile following exposure to 6OHDA.

Inflammation:

Recent theories suggest that death of nigrostriatal dopamine neurons in PD might be associated with inflammatory mechanisms. Thus, Compound 8 was assessed to determine whether ERβ agonist treatment might alter the inflammatory profile following bilateral 6OHDA lesions of the SN. ELISAs for tumor necrosis factor α (TNFα), monocyte chemotactic protein 1 (MCP-1 aka CCL2), interleukin-6 (IL-6), and interleukin-1β were conducted in peripheral blood mononuclear cells (PBMCs) and brain tissue homogenates from sham or 6OHDA treated animals. Preliminary studies showed that IL-6 and IL-1β were not detectable in PBMCs and were not elevated in brain homogenates. Both TNFα and MCP-1 were elevated in PBMCs from 6OHDA animals (data not shown). Thus, these two markers were chosen for further examination. In additional experiments, 6OHDA treatment was shown to result in elevated levels of TNFα in both brain and PBMCs. Treatment with Compound 8 prevented the rise in TNFα in both brain and PBMCs (FIG. 6). MCP-1 was elevated in PBMCs following 6OHDA when blood was taken on day 7 post-surgery, but not in brain homogenates taken on day 14 (following behavioral testing). The increase in MCP-1 in PBMCs was not prevented by Compound 8 treatment, even though the behavioral profile was normal. Thus, TNFα might be a maker of an inflammatory pathway triggered by 6OHDA infusion and prevented by treatment with an ERβ agonist in a manner that also prevents motor deficits and dopamine neuron loss in the substantia nigra.

Treatment of Chronic Inflammation with Compound 8

It was shown that Compound 8 may be used in an effective treatment of diseases characterized by chronic inflammatory responses. A well accepted model of chronic inflammation is the Complete Freund's adjuvant model (Gardell L R, Hyldtoft L, Del Tredici A L, Andersen C B, Fairbairn L C, Lund B W, Gustafsson M, Brann M R, Olsson R, Piu F. Differential modulation of inflammatory pain by a selective estrogen receptor beta agonist. Eur J. Pharmacol. 2008 Sep. 11; 592(1-3):158-9).

Rats were treated with Complete Freund's Adjuvant (CFA). After 4 days (upon reaching stable inflammation), CFA-treated animals were treated with 10 mg/kg subcutaneously (sc) of Compound 8, incomplete Freund's Adjuvant or vehicle, respectively. Responses were measured 24 hrs after drug administration. It is clear from the results shown in FIG. 8 that Compound 8 inhibits hyperalgesia and inflammation in the CFA model. FIG. 8 (A) shows the response to thermal hyperalgesia measured using the 52° C. hot plate test. Latencies, expressed in seconds (sec), were defined as the time needed for the animal to remove the treated paw from the hot surface. FIG. 8 (B) shows edema in the treated paw, was normalized to the change seen in the contralateral (untreated) paw.

Treatment of Chronic and Neuropathic Pain with Compound 8

It was shown that Compound 8 may be used in an effective treatment of diseases characterized by chronic and neuropathic pain. A well accepted model of neuropathic pain is the spinal nerve ligation model (Kim S H, Chung J M. An experimental model for peripheral neuropathy produced by segmental spinal nerve ligation in the rat. Pain. 1992 September; 50(3):355-63).

Spinal nerve ligation of the L5/L6 nerve was done as originally described by Kim and Chung, using male Sprague-Dawley rats. Allodynia was assessed by applying a light tactile stimulus (Von Frey hairs) to the plantar surface of the surgical paw until the 50% threshold is established. A positive response is recorded if the paw is sharply withdrawn. Eight VonFrey hairs were used (3.61, 3.84, 4.08, 4.31, 4.56, 4.74, 4.93 and 5.18). Compound 8 was administered s.c. Gabapentin was administered i.p. The results are shown in FIG. 9.

Above it has been shown that Compound 8 produces a number of beneficial effects in male rats with bilateral 6-OHDA lesions. Bilateral lesions were associated with motoric, cognitive and sensorimotor gating deficits, and all of these deficits were ameliorated by treatment with the ERβ agonist compounds Comparative compound 131 or Compound 8. Parallel to the behavioral findings, Comparative compound 131 and Compound 8 were found to prevent the loss of DA neurons in the SN. Interestingly these effects were not completely mimicked by the nonselective ER agonist estradiol. It is important to note that these effects were seen in male rats consistent with the potential of ERβ agonists to treat PD in both men and women.

The buccal/sublingual administration is a highly viable route for PD patients as quite a few are suffering from dysphagia. Compound 8 is showing good characteristics to be administrated via this route, good permeability in human cell tissue in vitro and good bioavalibility and overall PK characteristics in both rats and dogs. In addition, Compound 8 has shown good brain to plasma ratio in rats under a reasonable time span. Initial toxicity studies, both in vitro and in vivo, have shown that this compound is well tolerated; a 14 days toxicity study is in progress that will show the tolerated dose.

Compound 8 has also been shown to be effective in chronic inflammation and pain models. In addition to neuroprotection, selective ERβ agonist has also been shown to be efficient for indication such as depression, anxiety, pain, anosmia and hearing loss. Non-motor symptoms seen in PD patients, in addition, recently estrogens were suggested to regulate the degradation of α-synuclein (Cathepsin D) and the Aβ-peptide (Neprilysin and Insulin degrading enzyme) seen in Alzheimer's patients and early dementia PD or dementia with Lewy bodies.

Treatment of Allodynia Caused by a Chemotherapeutic Agent with Compound 8

This example uses another model of neuropathic pain, namely Taxol-induced neuropathy model, which is of particular interest because chemotherapy-related neuropathic pain represents a large, unmet medical need (Carlson K, Ocean A J. Peripheral neuropathy with microtubule-targeting agents: occurrence and management approach. Clin Breast Cancer. 2011 April; 11(2):73-81). Further, ERb-agonists may potentially be good anti-cancer drugs in their own right (Nilsson S, Koehler K F, Gustafsson J Å. Development of subtype-selective oestrogen receptor-based therapeutics. Nat Rev Drug Discov. 2011 Sep. 16; 10(10):778-92), and the face validity and relevance of this model to the human condition is very high given that the induction of neuropathy in humans and rats is achieved in essentially the same way.

Neuropathy was induced in male SD rats by 4×1 mg/kg consecutive daily doses of taxol as described (Naguib M, Diaz P, Xu J J, Astruc-Diaz F, Craig S, Vivas-Mejia P, Brown D L. MDA7: a novel selective agonist for CB2 receptors that prevents allodynia in rat neuropathic pain models. Br J. Pharmacol. 2008 December; 155(7):1104-16). The presence of tactile allodynia (von Frey filament 50% response threshold of <5 g) was confirmed prior to inclusion in the study. Drugs were administered sub-cutaneously (s.c.) except gabapentin was given intra-peritoneally (i.p.). Doses are given in mg/kg. * p<0.05.

Allodynia was assessed by applying a light tactile stimulus (Von Frey hairs) to the plantar surface of the surgical paw until the 50% threshold was established. A positive response was recorded if the paw was sharply withdrawn. Eight Von-Frey hairs were used (3.61, 3.84, 4.08, 4.31, 4.56, 4.74, 4.93 and 5.18). MPE (%) was calculated as $[(R_{drug}-R_{veh})/(R_{sham}-R_{veh})]*100\%$ where $R_{veh}$ was 4 and $R_{sham}$ was 13. Repeat dosing (FIG. 10C) was performed by administering the indicated doses of Compound 8 once daily via the s.c. route. Efficacy was measured 2 hours post-dose.

As shown in FIG. 10A Compound 8 reversed Taxol-induced allodynia in a dose-dependent manner, providing essentially complete reversal at doses of 10 and 30 mg/kg. In contrast, gabapentin was relatively ineffective in this model, with a maximum effect of 39% (FIG. 10B). Repeat dosing experiments demonstrated that the efficacy of Compound 8w as maintained over 5 days (FIG. 10C). ERb-selective agonists (DPN) were active in taxol-induced neuropathic pain, whereas ERa-selective (PPT) and non-selective estrogen receptor agonists (E2) were not (FIG. 10D). These studies demonstrate that Compound 8 is effective in a second neuropathic pain model.

The invention claimed is:

1. A compound of formula (I):

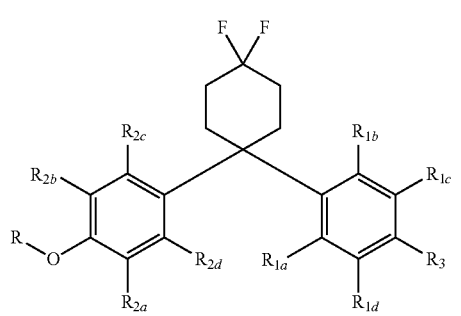

(I)

as one of a single isomer, a mixture of isomers and a racemic mixture of isomers; or one of a solvate and polymorph thereof, or one of a metabolite and prodrug thereof, or a pharmaceutically acceptable salt thereof, wherein, in the Formula (I), R is selected from the group consisting of hydrogen, $C_{1-6}$ alkyl, $C_{1-6}$ alkenyl, $C_{1-6}$ alkynyl, $C_{3-8}$ cycloalkyl, $C_{3-8}$ cycloalkenyl, substituted or unsubstituted $C_{3-8}$ aryl, substituted or unsubstituted $C_{3-8}$ heteroaryl, substituted or unsubstituted $C_{3-8}$ heteroalicyclyl, $C_{1-6}$ haloalkyl, sulfonyl, —C(=Z)R$_4$, —C(=Z)OR$_4$, —C(=Z)NR$_{4a}$R$_{4b}$, —S(O)NR$_{4a}$R$_{4b}$, —S(O)$_2$NR$_{4a}$R$_{4b}$, —P(=O)(OR$_4$ ), and —CH$_2$O(C=O)R$_4$, each of $R_{1a}$, $R_{1b}$, $R_{1c}$, and $R_{1d}$ are independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ alkyl($C_{3-6}$ cycloalkyl), halogen, $C_{1-6}$ haloalkyl, $C_{1-6}$ -haloalkoxy, —CN, —C(=Z)R$_4$, —C(=Z)OR$_4$, —C(=Z)NR$_{4a}$R$_{4b}$, —C(R$_4$)=NR$_{4a}$, —NR$_{4a}$R$_{4b}$, —N=CR$_{4a}$R$_{4b}$, —N(R$_4$)—C(=Z)R$_4$, —N(R$_4$)—C(=Z)NR$_{4a}$R$_{4b}$, —S(O)NR$_{4a}$R$_{4b}$, —S(O)$_2$NR$_{4a}$R$_{4b}$, —N(R$_4$)—S(=O)R$_4$, —N(R$_4$)—S(=O)$_2$R$_4$, —OR$_4$, —SR$_4$, and —OC(=Z)R$_4$, or two of $R_{1a}$, $R_{1b}$, $R_{1c}$, $R_{1d}$ and R$_3$ on adjacent carbons, taken together with the two intervening carbons to which they are attached, form one of a $C_{3-6}$ cycloalkenyl, aryl, heteroaryl and $C_{2-6}$ heterocycloalkyl group, each of $R_{2a}$, $R_{2b}$, $R_{2c}$ and $R_{2d}$ are independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ alkyl($C_{3-6}$ cycloalkyl), halogen, $C_{1-6}$ haloalkyl, $C_{1-6}$ haloalkoxy, —CN, —C(=Z)R$_4$, —C(=Z)OR$_4$, —C(=Z)NR$_{4a}$R$_{4b}$, —C(R$_4$)=NR$_{4a}$, —NR$_{4a}$R$_{4b}$, —N=CR$_{4a}$R$_{4b}$, —N( R$_4$)—C(=Z)R$_4$, —N(R$_4$)—C(=Z)NR$_{4a}$R$_{4b}$, —S(O)NR$_{4a}$R$_{4b}$, —S(O)$_2$NR$_{4a}$R$_{4b}$, —N(R$_4$)—S(=O)$_2$R$_4$, —OR$_4$,—SR$_4$, and—OC(=Z)R$_4$, or two $R_{2a}$, $R_{2b}$, $R_{2c}$ and $R_{2d}$ on adjacent carbons taken together with the two intervening carbons to which they are attached, form one of a $C_{3-6}$ cycloalkenyl, aryl, heteroaryl and $C_{2-6}$ heterocycloalkyl group, R$_3$ is selected from the group consisting of hydrogen, OR$_4$, $C_{1-6}$ alkyl, $C_{2-6}$ alkenyl, $C_{3-6}$ cycloalkyl, $C_{3-6}$ cycloalkenyl, halogen, —CN, —SR$_4$, sulfonyl, —NR$_{4a}$R$_{4b}$, and $C_{1-6}$ haloalkyl, each of R$_4$, R$_{4a}$ and R$_{4b}$ are independently selected from the group consisting of hydrogen, $C_{1-6}$ alkyl, $C_{2-6}$ alkenyl, $C_{2-6}$ alkynyl, $C_{3-6}$ cycloalkyl, $C_{3-6}$ cycloalkenyl, aryl, heteroaryl, and $C_{2-6}$ heterocycloalkyl, or R$_{4a}$ and R$_{4b}$ taken together with the nitrogen to which they are attached, form a $C_{2-6}$ heterocycloalkyl group, or R$_{4a}$ and R$_{4b}$ taken together with the carbon to which they are attached, form one of a $C_{3-6}$ cycloalkyl and $C_{2-6}$ heterocycloalkyl group, Z is one of O (oxygen) and S (sulfur), and wherein each of said alkyl, alkenyl, alkynyl, cycloalkyl, alkoxy cycloalkenyl, aryl, heteroaryl and $C_{2-6}$ heterocycloalkyl is independently optionally substituted by at least one substituent selected from the group consisting of —CN, halogen, haloalkyl, —O($C_{1-6}$ alkyl), —NR$_{4a}$R$_{4b}$, —S($C_{1-6}$ alkyl), and —O($C_{1-6}$ haloalkyl).

2. The compound according to claim 1, wherein

R is selected from the group consisting of hydrogen and $C_{1-6}$ alkyl, each of $R_{1a}$, $R_{1b}$, $R_{1c}$ and $R_{1d}$ are independently selected from the group consisting of hydrogen, $C_{1-6}$ alkyl, halogen, $C_{1-6}$ haloalkyl, —CN, and $C_{1-6}$ alkoxy, each of $R_{2a}$, $R_{2b}$, $R_{2c}$ and $R_{2d}$ are independently selected from the group consisting of hydrogen, $C_{1-6}$ alkyl, halogen, $C_{1-6}$ haloalkyl, —CN, and $C_{1-6}$ alkoxy, and R$_3$ is selected from the group consisting of hydrogen, $C_{1-6}$ alkyl, halogen, and $C_{1-6}$ haloalkyl.

3. The compound according to claim 1, wherein each of $R_{1a}$, $R_{1b}$, $R_{1c}$, and $R_{1d}$ are independently selected from the group consisting of hydrogen and halogen, each of $R_{2a}$, $R_{2b}$, $R_{2c}$ and $R_{2d}$ are independently selected from the group consisting of hydrogen and halogen, and R$_3$ is selected from the group consisting of hydrogen and halogen.

4. The compound according to claim 1, wherein one of $R_{1a}$ and $R_{1b}$ is halogen and the other of $R_{1a}$ and $R_{1b}$ is selected from the group consisting of hydrogen and halogen, each of $R_{1c}$ and $R_{1d}$ are independently selected from the group consisting of hydrogen and halogen, each of $R_{2a}$, $R_{2b}$, $R_{2c}$ and $R_{2d}$ are independently selected from the group consisting of hydrogen and halogen, and

43

$R_3$ is selected from the group consisting of hydrogen and halogen.

5. The compound according to claim 1, wherein the halogen is independently selected from the group consisting of chlorine, bromine and fluorine.

6. The compound according to claim 1, wherein R is one of hydrogen and methyl.

7. The compound according to claim 1, wherein
one of $R_{1a}$ and $R_{1b}$ is one of fluorine and chlorine and the other of $R_{1a}$ and —$R_{1b}$ is hydrogen,
each of $R_{1c}$ and $R_{1d}$ are hydrogen,
one of $R_{2a}$ and $R_{2b}$ is halogen and the other of $R_{2a}$ and $R_{2b}$ is hydrogen,
$R_{2c}$ and $R_{2d}$ are hydrogen, and
$R_3$ is hydrogen.

8. The compound according to claim 7, wherein one of $R_{2a}$ and $R_{2b}$ is fluorine and the other of $R_{2a}$ and $R_{2b}$ is hydrogen.

9. The compound of claim 1, wherein the compound is selected from the group consisting of:

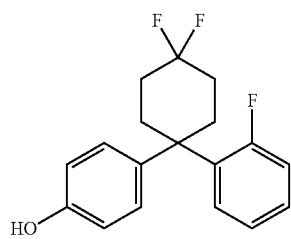

8

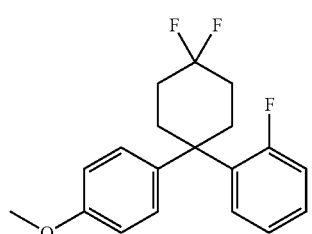

9

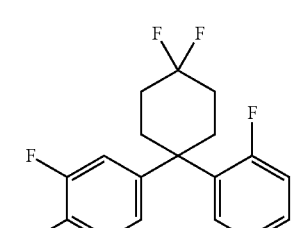

10

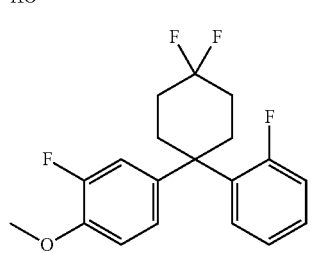

11

44

-continued

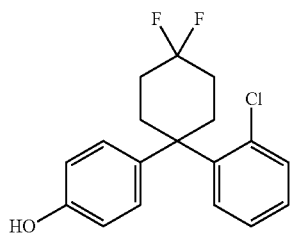

12

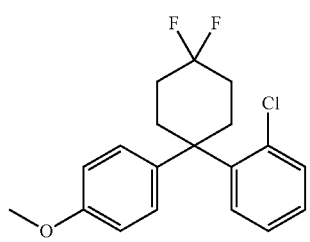

13

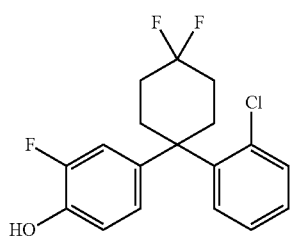

14

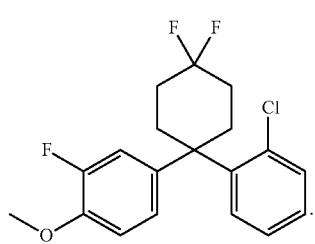

15

10. The compound according to claim 9, wherein the compound is selected from the group consisting of compound 8, compound 9 and compound 10.

11. A pharmaceutical composition comprising:
a pharmaceutically acceptable amount of a compound of claim 1; and
at least one of a physiologically acceptable carrier, diluent and excipient.

12. The compound according to claim 1, wherein
one of $R_{1a}$ and $R_{1b}$ is one of fluorine and chlorine and the other of $R_{1a}$ and $R_{1b}$ is hydrogen,
each of $R_{1c}$ and $R_{1d}$ are hydrogen,
each of $R_{2a}$, $R_{2b}$, $R_{2c}$, and $R_{2d}$ are hydrogen, and
$R_3$ is hydrogen.

* * * * *